United States Patent
Kavounas

(10) Patent No.: US 11,065,464 B2
(45) Date of Patent: *Jul. 20, 2021

(54) METHODS FOR WEARABLE SYSTEM

(71) Applicant: West Affum Holdings Corp., Grand Cayman (KY)

(72) Inventor: Gregory T. Kavounas, Bellevue, WA (US)

(73) Assignee: West Affum Holdings Corp., Grand Cayman (KY)

( * ) Notice: Subject to any disclaimer, the term of this patent is extended or adjusted under 35 U.S.C. 154(b) by 47 days.

This patent is subject to a terminal disclaimer.

(21) Appl. No.: 16/004,370

(22) Filed: Jun. 9, 2018

(65) Prior Publication Data
US 2018/0289975 A1    Oct. 11, 2018

Related U.S. Application Data

(60) Division of application No. 14/788,614, filed on Jun. 30, 2015, now Pat. No. 10,016,613, which is a continuation-in-part of application No. 13/906,327, filed on May 30, 2013, now Pat. No. 9,827,431.

(60) Provisional application No. 61/807,453, filed on Apr. 2, 2013.

(51) Int. Cl.
*A61N 1/39* (2006.01)
*A61N 1/04* (2006.01)
(Continued)

(52) U.S. Cl.
CPC .............. *A61N 1/3925* (2013.01); *A61B 5/25* (2021.01); *A61B 5/6831* (2013.01);
(Continued)

(58) Field of Classification Search
CPC ......... A61N 1/3925; A61N 1/39; A61N 1/046
See application file for complete search history.

(56) References Cited

U.S. PATENT DOCUMENTS

| | | |
|---|---|---|
| 3,724,355 A | 4/1973 | Unger |
| 3,724,455 A | 4/1973 | Unger |
| (Continued) | | |

FOREIGN PATENT DOCUMENTS

WO    1998039061 A2    9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — William J Levicky
(74) *Attorney, Agent, or Firm* — Spectrum IP Law Group LLC

(57) ABSTRACT

A wearable system includes a support structure with optionally one or more electrodes in an unbiased state. Different sensor modules may monitor, for the long-term, different patient parameters such as the patient's motion, a physiological parameter, a patient sound etc., other than the patient's ECG. The sensor modules can be worn by the patient concurrently, or only one at a time as convenient, and may provide respective sensor signals. The system may determine from one or more of the available received signals whether a certain threshold has been reached, such as when the patient is having an actionable episode. If so, at least one electrode may become mechanically biased against the patient's body, for making good electrical contact. Then, an ECG reading may be taken and/or therapy may be administered.

26 Claims, 22 Drawing Sheets

WEARABLE DEFIBRILLATOR SYSTEM

(51) Int. Cl.
*A61B 5/00* (2006.01)
*A61B 5/25* (2021.01)
*A61B 7/00* (2006.01)
*A61B 5/0205* (2006.01)

(52) U.S. Cl.
CPC ............ *A61B 5/6843* (2013.01); *A61N 1/046* (2013.01); *A61N 1/3904* (2017.08); *A61N 1/3968* (2013.01); *A61N 1/3993* (2013.01); *A61B 5/0205* (2013.01); *A61B 7/00* (2013.01)

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,928,690 A * | 5/1990 | Heilman ............... A61N 1/3904 607/4 |
| 4,955,381 A | 9/1990 | Way et al. |
| 5,078,134 A | 1/1992 | Heilman et al. |
| 5,201,992 A | 4/1993 | Andreadakis et al. |
| 5,228,449 A | 7/1993 | Christ et al. |
| 5,348,008 A * | 9/1994 | Bornn ................ A61B 5/0006 600/523 |
| 5,353,793 A | 10/1994 | Bornn |
| 5,356,785 A | 10/1994 | McMahon et al. |
| RE34,800 E | 11/1994 | Hutchins |
| 5,394,892 A | 3/1995 | Kenny |
| 5,405,362 A | 4/1995 | Kramer et al. |
| 5,425,749 A | 6/1995 | Adams |
| 5,474,574 A | 12/1995 | Payne et al. |
| 5,630,834 A | 5/1997 | Bardy |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,141,588 A * | 10/2000 | Cox .................... A61N 1/37211 607/9 |
| 6,148,233 A | 11/2000 | Owen et al. |
| 6,201,992 B1 | 3/2001 | Freeman |
| 6,208,894 B1 * | 3/2001 | Schulman .......... A61N 1/37252 607/2 |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,473,638 B2 | 10/2002 | Ferek-Petric |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 6,941,168 B2 | 9/2005 | Girouard |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,086,320 B2 | 12/2011 | Benjamin |
| 8,135,462 B2 | 3/2012 | Owen et al. |
| 8,140,154 B2 | 3/2012 | Donnelly et al. |
| 8,271,082 B2 | 9/2012 | Donnelly et al. |
| 8,323,189 B2 | 12/2012 | Tran et al. |
| 8,369,944 B2 | 2/2013 | Macho et al. |
| 8,437,824 B2 | 5/2013 | Moon et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 9,757,579 B2 | 9/2017 | Foshee, Jr. et al. |
| 9,827,431 B2 | 11/2017 | Chapman et al. |
| 10,426,966 B2 | 10/2019 | Foshee, Jr. et al. |
| 10,543,375 B2 | 1/2020 | Chapman et al. |
| 2003/0158593 A1 | 8/2003 | Heilman et al. |
| 2004/0220623 A1 | 11/2004 | Hess |
| 2005/0107833 A1 | 5/2005 | Freeman et al. |
| 2005/0107834 A1 | 5/2005 | Freeman et al. |
| 2006/0017575 A1 | 1/2006 | McAdams |
| 2007/0179539 A1 | 8/2007 | DeGroot et al. |
| 2008/0312709 A1 | 12/2008 | Volpe et al. |
| 2009/0005827 A1 | 1/2009 | Weintraub et al. |
| 2009/0018595 A1 | 1/2009 | Bharmi et al. |
| 2009/0076579 A1 | 3/2009 | Libbus et al. |
| 2009/0326339 A1 | 12/2009 | Horvitz |
| 2010/0007413 A1 | 1/2010 | Herleikson |
| 2010/0298899 A1 | 11/2010 | Donnelly et al. |
| 2010/0331904 A1 | 12/2010 | Warren et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0302860 A1 | 2/2012 | Tiu, Jr. et al. |
| 2012/0109687 A1 * | 5/2012 | Tubb ................ A61B 5/14532 705/3 |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158074 A1 | 6/2012 | Hall |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0310315 A1 | 12/2012 | Savage et al. |
| 2013/0012151 A1 | 1/2013 | Hankins |
| 2013/0085538 A1 | 4/2013 | Volpe et al. |
| 2013/0218252 A1 | 8/2013 | Kaib et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0025132 A1 | 1/2014 | Libbus et al. |
| 2014/0070957 A1 | 3/2014 | Longinotti-Buitoni et al. |
| 2014/0073979 A1 * | 3/2014 | Inciardi ............... A61B 5/0022 600/509 |
| 2014/0088739 A1 | 3/2014 | Ellis et al. |
| 2014/0091937 A1 | 4/2014 | Pratt et al. |
| 2014/0150781 A1 | 6/2014 | Capua et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |

OTHER PUBLICATIONS

Lifecor LifeVest System Model WCD 3100 Operator's Manual, 2006, PN 20B0040 Rev FI, Zoll Lifecor Corporation, Pittsburgh, PA.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

(56) References Cited

OTHER PUBLICATIONS

LifeVest Model 4000 Patient Manual, Zoll, 2009, PN 20B0047 Rev B.
Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

WEARABLE DEFIBRILLATOR SYSTEM

FIG. 2 — SAMPLE THRESHOLDS FOR MAKING DECISIONS

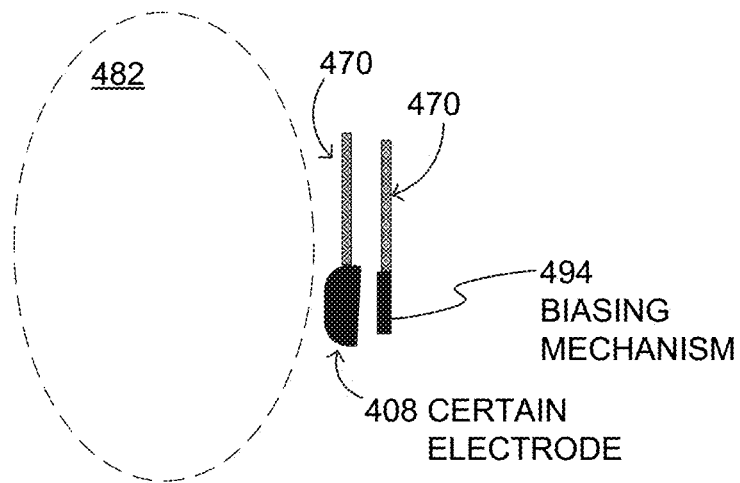
FIG. 4A  *ELECTRODE UNBIASED TOWARDS BODY*
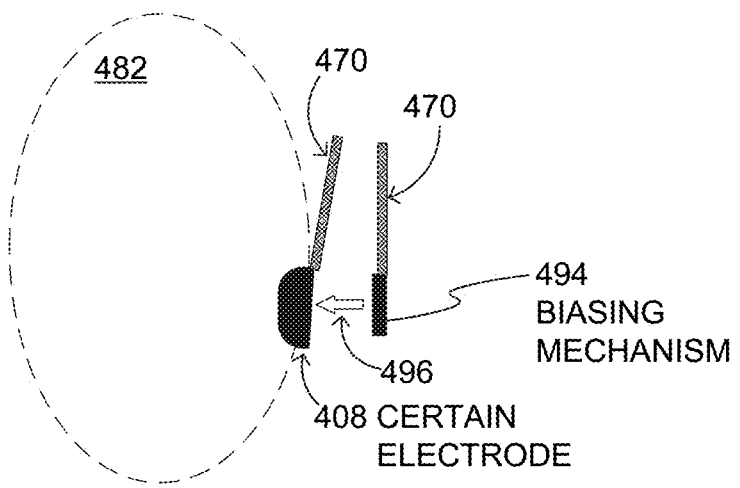
FIG. 4B  *ELECTRODE BIASED TOWARDS BODY*

*METHODS*

*METHOD OPERATIONS*

700

| 747 RECORD INDICATION OF ELECTRODE BECOMING BIASED |

*METHOD OPERATIONS*

*METHOD OPERATIONS*

*METHODS*

*METHODS*

MULTIPLE SIGNALS

METHODS

2340

| SCENARIO | S1 ALARM? | S2 ALARM? | S3 ALARM? | CERTAIN SEVERITY THRESOLD REACHED? |
|---|---|---|---|---|
| 1 | NO | NO | NO | NO |
| 2 | YES | NO | NO | YES |
| 3 | NO | YES | NO | YES |
| 4 | NO | NO | YES | YES |

FIG. 23

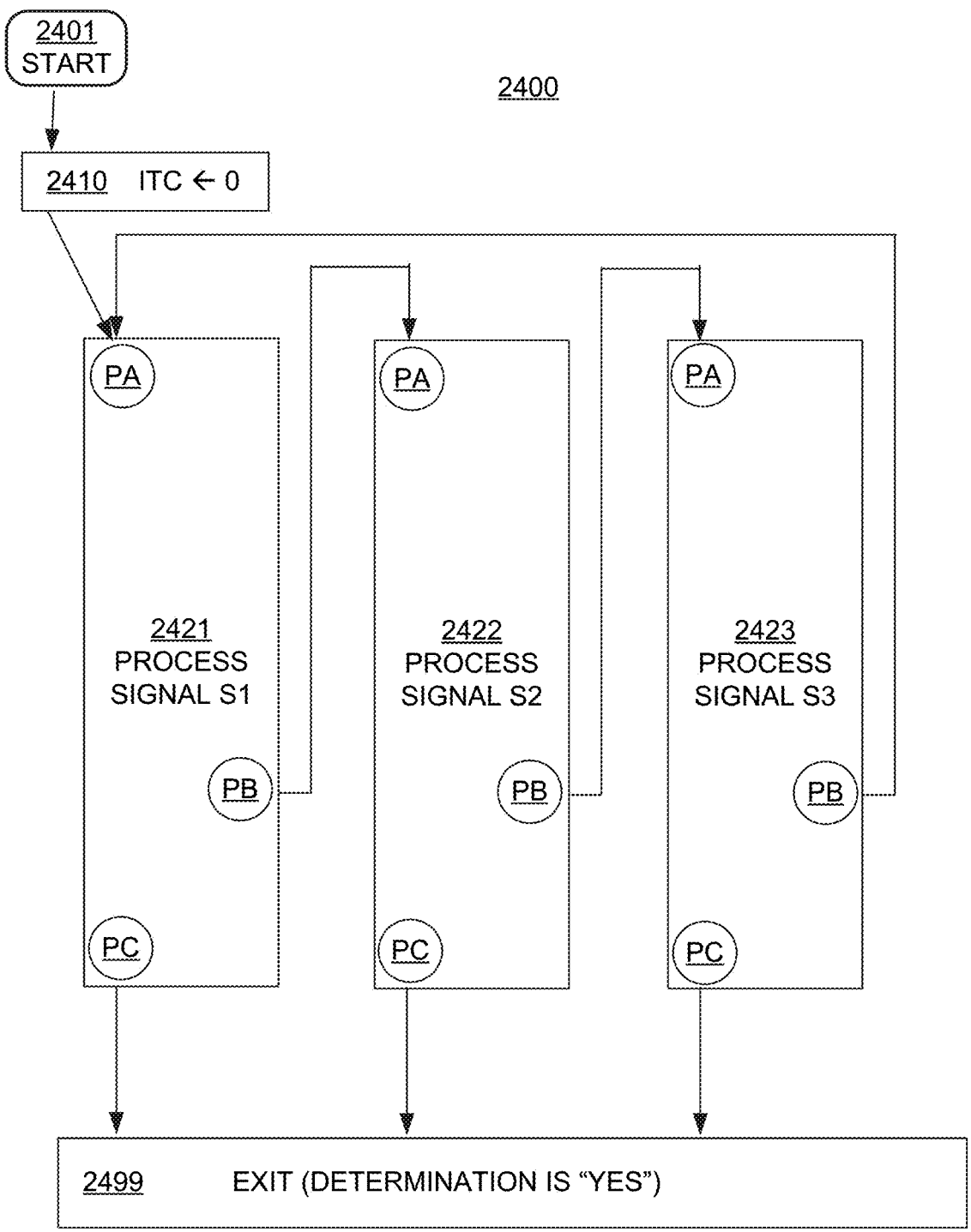
FIG. 24    METHODS

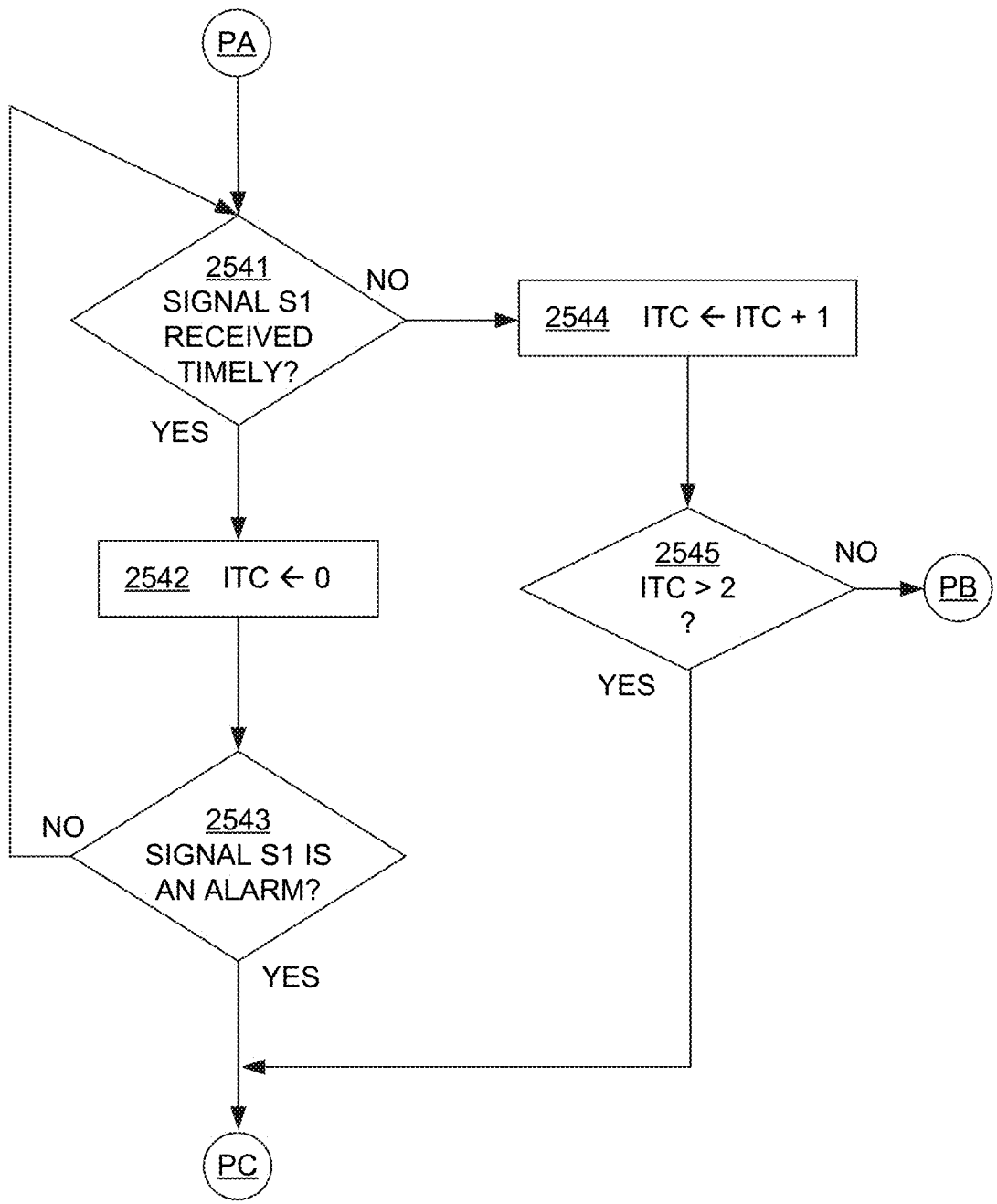
FIG. 25   *METHODS*

METHODS FOR WEARABLE SYSTEM

CROSS REFERENCE TO RELATED PATENT APPLICATIONS

This patent application is a divisional of U.S. patent application Ser. No. 14/788,614 filed on Jun. 30, 2015, which in turn is a Continuation-In-Part of U.S. patent application Ser. No. 13/906,327, filed on May 30, 2013 and issued as U.S. Pat. No. 9,827,431, which in turn claims priority from U.S. Provisional Patent Application Ser. No. 61/807,453, filed on Apr. 2, 2013.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include individuals who have had a heart attack, or a prior SCA episode. A frequent recommendation is for these people to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardiac defibrillator ("WCD") system. A WCD system typically includes a harness, vest, or other garment that the patient is to wear. The WCD system includes a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

A problem is that compliance by the patient is often not full. While the patient has the system, they often do not wear it because they find it cumbersome and uncomfortable. The issue of improving compliance has been addressed, for example in US Patent Application No. 20120283794.

A root of the discomfort is from the fact that the electrodes of the wearable system have to be making good electrical contact continuously with the patient's skin, so that the patient's ECG can be monitored continuously. The problem has been addressed, for example in U.S. Pat. No. 6,546,285, titled LONG TERM WEAR ELECTRODE FOR DEFIBRILLATION SYSTEM. The latter patent teaches, among other things, to move the electrodes to different places on the patient's skin at different times, and/or to use a hydrogel for the electrodes that includes a therapeutic agent which promotes skin health.

BRIEF SUMMARY

The present description gives instances of Wearable Cardiac Defibrillator (WCD) systems, storage media that store programs, and methods, the use of which may help overcome problems and limitations of the prior art.

In one embodiment, a Wearable Cardiac Defibrillator (WCD) system includes a support structure with one or more electrodes in an unbiased state. Different sensor modules may monitor, for the long-term, different patient parameters. The parameters can be the patient's motion, a physiological parameter, etc., other than the patient's ECG. The sensor modules can be worn by the patient concurrently, or only one at a time, and may provide respective sensor signals. A sensor interface may receive the available signals, and a processor may determine from one or more of the received signals whether a certain threshold has been reached, such as when the patient is having an actionable episode. If so, at least one electrode may become mechanically biased against the patient's body, for making good electrical contact. Then, an ECG reading may be taken and/or electrical therapy may be administered, such as defibrillation or pacing.

An advantage over the prior art is that, while the wearable defibrillator system does require long-term wearing to protect the patient, wearing itself does not require that one or more of its electrodes be making good electrical contact with the patient's skin for the long term. The contact is made by the biasing, when the system otherwise detects that the patient is having an actionable episode. Until then, however, the electrodes can be worn more loosely, and thus feel more similar with how loose the other garments feel to the wearer. This can reduce the patient's aversion to wearing the defibrillation system, who might in turn comply more with the instruction to wear it. Moreover, the patient is able to switch between wearing different sensor modules as is convenient for each sensor module, given the circumstances at the time. For example, if they are planning to sleep, they could choose one or more modules that are most comfortable for sleeping but might not be good for other daily activities. If they are concerned about appearance, they could choose one or more modules that are easy to conceal. If they are planning to exercise, they could choose one or more modules that are compatible with their planned activity.

These and other features and advantages of this description will become more readily apparent from the Detailed Description, which proceeds with reference to the associated drawings in which:

BRIEF DESCRIPTION OF THE DRAWINGS

FIG. 4A is a diagram showing an electrode, such as a possible embodiment of an electrode of FIG. 1, which is not being biased towards the body of the wearer according to embodiments.

FIG. 4B is a diagram showing the electrode of FIG. 4A, but in which the electrode is instead being biased towards the body of the wearer according to embodiments.

FIG. 23 is a sample truth table for an operation of the method of FIG. 22 according to embodiments.

FIG. 24 is a flowchart for illustrating a sample method for performing operations of the method of FIG. 22 according to embodiments.

FIG. 25 is a flowchart for illustrating a sample method for performing an operation of the method of FIG. 24 according to embodiments.

DETAILED DESCRIPTION

As has been mentioned, the present description is about Wearable Cardiac Defibrillator (WCD) systems, storage media that store programs, and methods. Embodiments are now described in more detail.

Embodiments include WCD systems, which are configured to be worn by a person. A WCD system made according to embodiments has a number of components. These components can be provided separately as modules that can be interconnected, or can be combined with other components, etc.

The person wearing the WCD system is sometimes called also a patient and/or a wearer. The person may be moving, for example during their daily activities. As they move, any garments they wear may shift with respect to their body. The wearable defibrillator systems of the embodiments are configured to defibrillate the patient by delivering electrical charge to the patient's body.

A component of a WCD system can be a support structure, which is configured to be worn by the patient. The support structure can be any structure suitable for wearing, such as a harness, a vest, a half-vest—for example over the left side of the torso that positions electrodes on opposite sides of the heart, one or more belts that are configured to be worn horizontally or possibly vertically over a shoulder, another garment, and so on. The support structure can be implemented in a single component or multiple components. For example, a support structure may have a top component resting on the shoulders, for ensuring that the defibrillation electrodes will be in the appropriate positions for defibrillating, and a bottom component resting on the hips, for carrying the bulk of the weight of the defibrillator. A single component embodiment could be with a belt around at least the torso. Other embodiments could use an adhesive structure or another way for attaching to the patient, without encircling any part of the body. There can be other examples.

Figure 1:
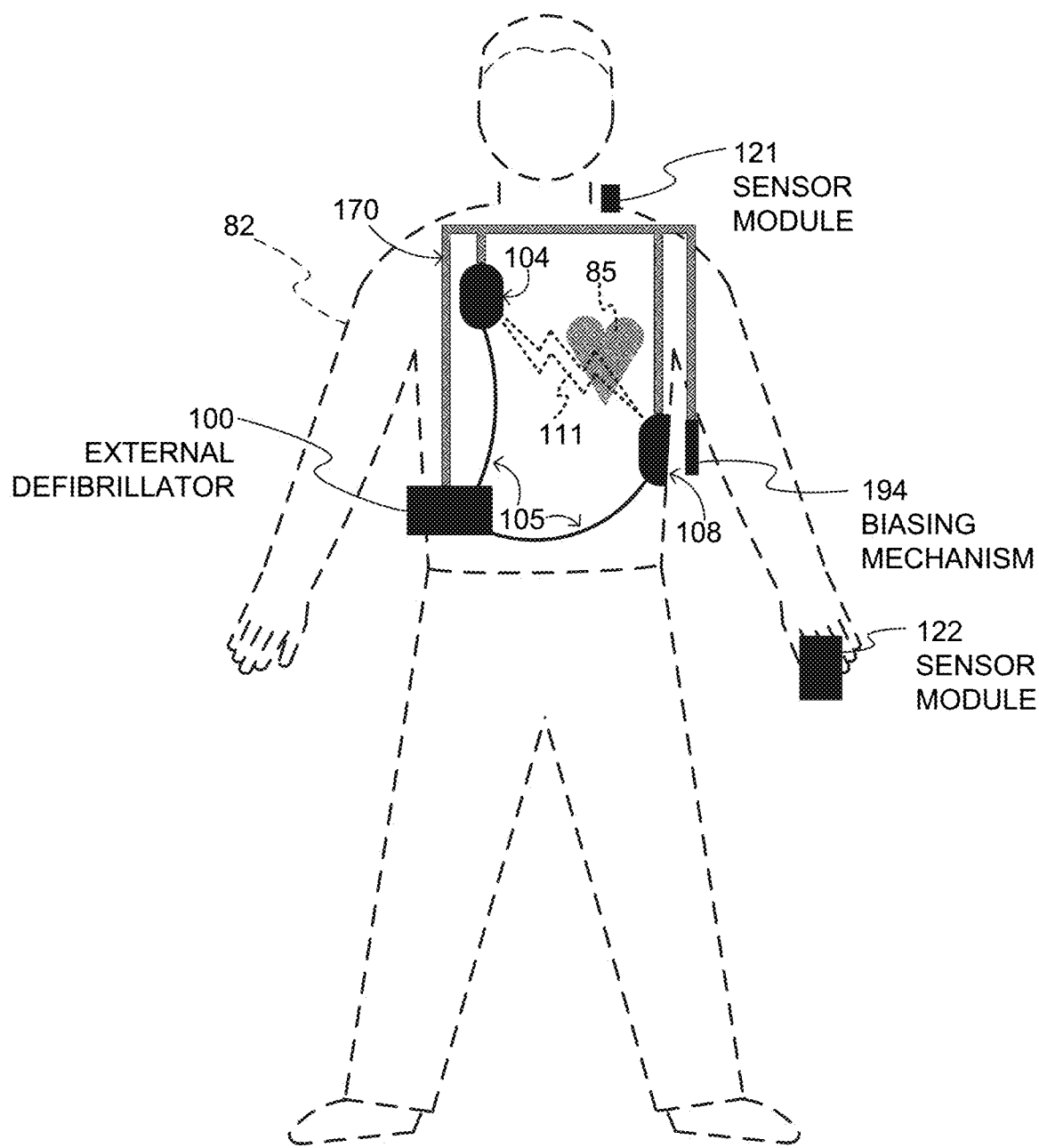
FIG. 1 is a diagram of components of a sample Wearable Cardiac Defibrillator (WCD) system, made according to embodiments.

FIG. 1 depicts components of a WCD system made according to embodiments, as it might be worn by a person 82. In FIG. 1, a generic support structure 170 is shown relative to the body of patient 82, and thus also relative to his or her heart 85. Structure 170 could be a harness, a vest, a half-vest, one or more belts, or a garment, etc., as per the above. Structure 170 could be implemented in a single component, or multiple components, and so on. Structure 170 is wearable by patient 82, but the manner of wearing it is not depicted, as structure 170 is depicted only generically in FIG. 1.

WCD systems according to embodiments may be further configured for use with one or more sensor modules. By way of an example, sensor modules 121, 122 are shown in FIG. 1, and both are being used by patient 82. Additional sensor modules may be provided, such as a third one, a fourth one, etc., some of which are used at different times. Such sensor modules can be motion sensors, physiological parameter sensors, etc., and be used for determining whether intervention by the WCD system is desired. A WCD system according to embodiments may further include a sensor interface (not shown in FIG. 1) configured to receive signals from sensor modules 121, 122. Embodiments of sensor modules and sensor interfaces are described in more detail later in this document.

Figure 2:
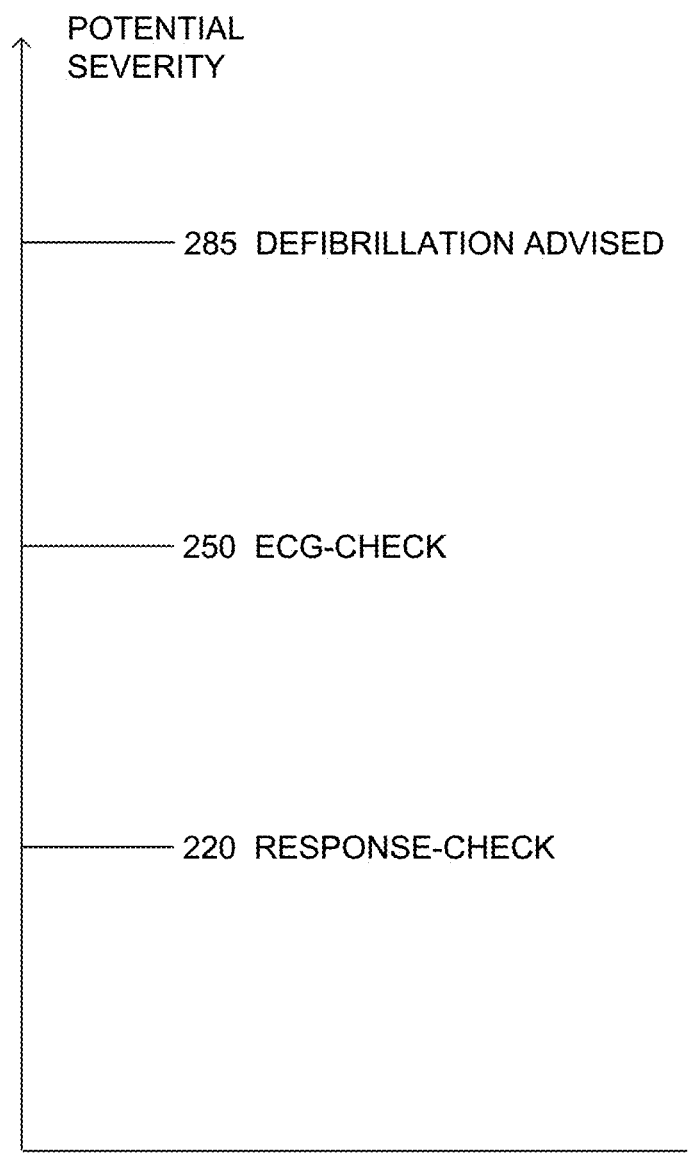
FIG. 2 is a diagram showing sample thresholds for making decisions according to embodiments.

FIG. 2 is a diagram showing possible thresholds 220, 250, 285 for making decisions according to embodiments. These thresholds 220, 250, 285 may also be called severity thresholds. Examples of use of these thresholds are described later in this document, also in terms of flowcharts. It will be appreciated that not all of these thresholds need be used in every embodiment.

Thresholds 220, 250, 285 are shown on a single scale, according to relative potential severity of the patient's condition. Even though shown in a single scale, it should be remembered that these thresholds may be established for the same or different patient parameters, for use by the same or different elements of embodiments. For example, the thresholds can be either for the parameter monitored by the sensor module, or by another sensor module, or for an ECG reading of the patient obtained by electrodes, and so on. Moreover, there can be same or different results if the thresholds are reached or exceeded.

The thresholds of FIG. 2 are shown in a scale. Embodiments may escalate the checking and operations, such as along this scale, as they detect the patient's condition to be more severe, in ways that the system could address by administering electrical therapy.

These thresholds are now described in more detail. Threshold 220 is a response-check threshold, above which the decision can be that the patient be asked to respond, in some manner, as to whether they are fine. A patient who responds they are fine will likely not need electrical therapy at this time. Threshold 250 is an ECG-check threshold, above which the decision can be that an ECG reading of the patient needs to be taken for certainty. If the patient's ECG turns out to be a non-shockable rhythm, such as a normal sinus rhythm, then the system need not administer electrical therapy. Threshold 285 is a defibrillation advised threshold, above which a defibrillate decision is made, and the patient is defibrillated. Below the lowest of thresholds, which in FIG. 2 is threshold 220, the patient can be presumed to be not in danger, and the decision can be that no action is taken, and there is no further escalation.

In terms of levels, it is known how to infer the activities and likely severity of the patient condition by interpreting signals from a sensor module that includes a motion sensor. Such signals may be indicative of motion of the patient. For example, if the patient stops moving at a time when they are expected to be moving or continue moving, or exhibits other behavior that indicates that SCA may be taking place, that can be cause for escalation to a higher level, as per the above. As such, the threshold can sometimes be adjusted according to an output of the motion detector itself.

The thresholds can be adjusted also with regard to additional parameters that can be monitored. One such additional parameter can be the time of day, which can be monitored by a clock in a processor of the system. For example, the patient is expected to be sleeping during more of the night hours.

In other embodiments, the monitored parameter is a physiological parameter of the patient. The physiological parameter can be any one that would help detect whether the patient is in need of electrotherapy by the wearable defibrillation system, and examples are given later in this document.

Systems according to embodiments may also include a capacitor, which can be configured to store an electrical charge. Under certain circumstances, the charge is configured to be delivered to the patient's body according to embodiments. Preferably the capacitor is coupled to the support structure, and the charge is delivered while the patient is wearing the support structure.

In certain embodiments, the capacitor is implemented as part of a defibrillator, such as sample external defibrillator 100 in FIG. 1. In those cases, the defibrillator can be coupled to the support structure, such as defibrillator 100 is coupled to structure 170 in FIG. 1. In other embodiments, a full defibrillator may not be implemented, such as in instances where the capacitor charge is controlled to be delivered to the patient remotely, and so on.

Figure 3:
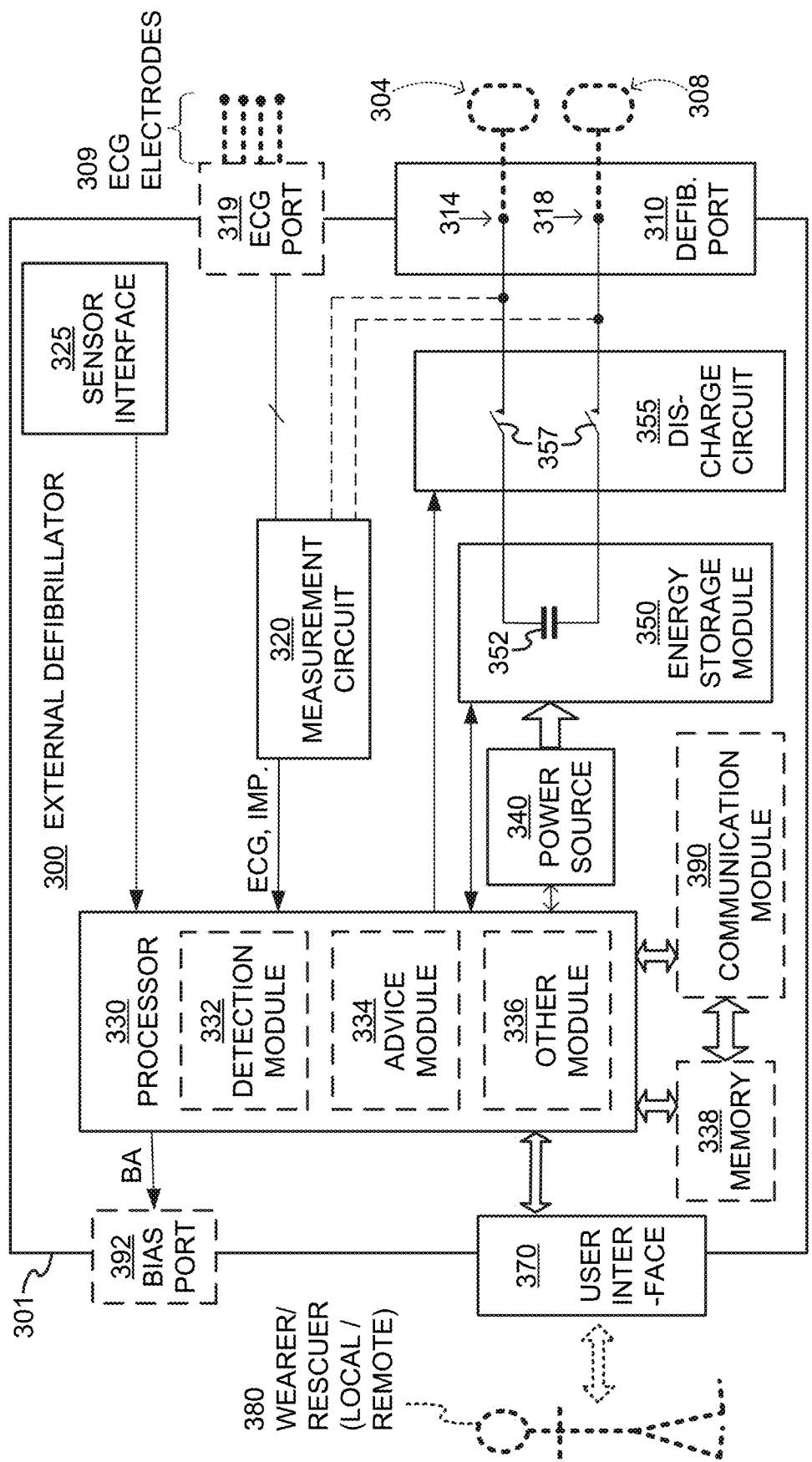
FIG. 3 is a diagram showing sample components of an external defibrillator, such as the one belonging in the system of FIG. 1, and which is made according to embodiments.

FIG. 3 is a diagram showing components of an external defibrillator 300 made according to embodiments. These components can be, for example, in external defibrillator 100 of FIG. 1, in the event that defibrillator components beyond the capacitor are provided. These components of FIG. 3 can be provided in a housing 301, which is also known as defibrillator housing 301 and casing 301. As seen from FIG. 1, defibrillator housing 301 can be configured to be coupled to the support structure.

External defibrillator 300 is intended for patient 380 who would be the wearer, such as person 82 of FIG. 1. In the shown embodiment, defibrillator 300 includes the above-mentioned sensor interface 325. It will be understood that sensor interface 325 need not be touching housing 301 if the signals from the sensor modules arrive wirelessly, but may protrude through housing 301 otherwise. In other embodiments, the sensor interface is provided outside housing 301.

Defibrillator 300 typically includes a defibrillation port 310, such as a socket in housing 301. Defibrillation port 310 includes nodes 314, 318. Defibrillation electrodes 304, 308, which will be described later in more detail, can be plugged in defibrillation port 310, so as to make electrical contact with nodes 314, 318, respectively. It is also possible that defibrillation electrodes can be connected continuously to defibrillation port 310, instead. Either way, defibrillation port 310 can be used for guiding via electrodes to the wearer the electrical charge that has been stored in energy storage module 350.

Defibrillator 300 may optionally also have an ECG port 319 in housing 301, for plugging in ECG electrodes 309, which are also known as ECG leads. It is also possible that ECG electrodes can be connected continuously to ECG port 319, instead. ECG electrodes 309 can help sense an ECG signal, e.g. a 12-lead signal, or a signal from a different number of leads, as long as they make good electrical contact with the body of the patient.

Defibrillator 300 also includes a measurement circuit 320. Measurement circuit 320 receives physiological signals from ECG port 319, if provided. Even if defibrillator 300 lacks ECG port 319, measurement circuit 320 can obtain physiological signals through nodes 314, 318 instead, when defibrillation electrodes 304, 308 are attached to the patient. In these cases, a patient's ECG signal can be sensed as a voltage difference between electrodes 304, 308. Plus, impedance between electrodes 304, 308 can be sensed for detecting, among other things, whether these electrodes 304, 308 are not making good electrical contact with the patient's body. These physiological signals are sensed, and information about them is rendered by circuit 320 as data, or other signals, etc.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAS), Programmable Logic Devices (PLDs), Application Specific Integrated Circuits (ASICs), any combination of one or more of these, and so on.

Processor 330 can be considered to have a number of modules. One such module can be a detection module 332. Processor 330, running detection module 332, is a sample embodiment of a logic device configured to determine whether the above-described monitored parameter has reached a specific threshold. For example, the monitored parameter can be input from sensor modules 121, 122, or others if provided. For another example, detection module 332 can include a Ventricular Fibrillation ("VF") detector and the patient's sensed ECG from measurement circuit 320 can be used to determine whether the patient is experiencing VF. Detecting VF is useful, because VF is a precursor to SCA.

Another such module in processor 330 can be an advice module 334, which arrives at advice, for example based on outputs of detection module 332, and/or implements decisions. There can be many types of advice according to embodiments. As one example, a Shock Advisory Algorithm can render the advice to shock, as opposed to not shock the patient. Such can be, for example, when the patient's condition has reached or exceeded defibrillation advised threshold 285 of FIG. 2. Shocking can be for defibrillation, pacing, and so on. If the advice is to shock, some external defibrillator embodiments proceed with shocking, or may advise a remote attendant to do it, and so on. As another example, the advice can be to administer CPR, and defibrillator 300 may further issue prompts for it, and so on.

One more example of a decision that can be made is to bias one or more electrodes towards the patient's body, as will be described later in this document. The decision can be communicated in some of these embodiments by generating a biasing signal BA. Defibrillator 300 optionally includes also a bias port 392 for exporting biasing signal BA from bias port 392 to a biasing mechanism of the system, which will also be described later.

Processor 330 can include additional modules, such as module 336, for other functions. In addition, processor 330 may perform the functions of interpreting the signals received from the sensor modules.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for person 380, if they are a local rescuer. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include an AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes a capacitor 352, which can be a single capacitor or a system of capacitors, and so on. As described above, capacitor 352 can store the charge for delivering to the patient.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for a user 380. User 380 can be the wearer, if conscious, or a rescuer. The rescuer can be local, such as a bystander who might offer assistance, or a trained person who might arrive after the fact. Alternately the rescuer could be remote, such as a trained person in remote communication with a system according to embodiments, and/or with the wearer.

User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, touchscreens, a microphone, and so on. In addition, discharge circuit 355 can be controlled by processor 330, or directly by user 380 via user interface 370, and so on.

Defibrillator 300 can optionally include other components. For example, a communication module 390 may be provided for communicating with other machines or a remote rescuer 380. Such communication can be performed wirelessly, or via wire, or by infrared communication, and so on. This way, data can be communicated, such as patient data, episode information, therapy attempted, CPR performance, and so on. In some embodiments, communication module 390 performs the functions of the sensor interface, and sensor interface 325 is not provided separately as shown.

Embodiments of the system of the invention may additionally include defibrillation electrodes. It will be appreciated that the defibrillation electrodes of embodiments could both deliver a charge, and also serve for sensing the patient's ECG. The defibrillation electrodes can deliver to the patient electrical charge stored in the capacitor, for restoring their heart rhythm, when the defibrillation electrodes make good electrical contact with the body of the wearer.

FIG. 1 shows an example of defibrillation electrodes 104, 108, which are coupled to external defibrillator 100 via electrode leads 105. When defibrillation electrodes 104, 108 make good electrical contact with the body of person 82, defibrillator 100 can administer, via electrodes 104, 108, a brief, strong electric pulse 111 through the body. Pulse 111, also known as a defibrillation shock, goes also through heart 85, in an attempt to restart it, for saving the life of patient 82.

In the example of FIG. 3, defibrillation electrodes 304, 308 would plug into defibrillation port 310, so as to make electrical contact with nodes 314, 318, respectively. Defibrillation electrodes 304, 308 could be similar to defibrillation electrodes 104, 108 of FIG. 1.

Embodiments of the system of the invention may additionally include ECG electrodes. If provided, ECG electrodes could be electrically connected for example as seen in FIG. 3 for ECG electrodes 309.

As such, in many embodiments, either defibrillation electrodes are provided by themselves, or ECG electrodes are provided in addition to defibrillation electrodes. An ECG reading can be provided by either type of electrodes, preferably while they are making good electrical contact with the body of the patient, and more particularly the skin.

In a number of embodiments, all the above mentioned electrodes are not always making good electrical contact with the patient's skin. In fact, at least one of the above-mentioned electrodes, also known as a certain electrode, can be coupled to the support structure such that, while the support structure is worn by the patient, the certain electrode is at a so-called unbiased state. When in the unbiased state, the certain electrode is moveable with respect to the patient's body, for example as a result of the patient's moving around. For example, the certain electrode could contact the patient's skin as a regular garment does, for example as does a shirt that is not tightened around the patient's body. As such the certain electrode could shift around the patient's skin, and occasionally lose contact with it. In those occasional moments, the electrical impedance between the certain electrode and the patient's skin would become infinite.

As will be seen below, the certain electrode can be either one of the defibrillation electrodes, or one of the ECG electrodes, if provided. Of course, what is written about the certain electrode could also apply for a companion electrode that performs a similar function.

It is that lack of the certain electrode's making consistently good electrical contact with the skin that makes the support structure more comfortable to wear than the prior art for the long term. Of course, the certain electrode not necessarily making consistently good electrical contact for the long term is not desirable, but that will be addressed by the biasing mechanism that is now described.

Embodiments of the system of the invention may additionally include a first biasing mechanism. The first biasing mechanism can be configured to cause the certain electrode to transition from the above described unbiased state to a so-called biased state. When in the biased state, the certain electrode is biased towards the patient's body against the support structure. The biasing, then, is by a force that causes the certain electrode to be less moveable with respect to the patient's body than when in the unbiased state. As such, when in the biased state, the certain electrode makes better and/or more reliable electrical contact with the patient's skin than in the unbiased state. The better electrical contact can be used for more reliable defibrillation and or receiving ECG signals, as the case may be for the certain electrode.

In preferred embodiments, the first biasing mechanism can cause the certain electrode to transition from the unbiased state to the biased state, responsive to a value of the monitored parameter reaching a threshold. As such, the first biasing mechanism can be configured to receive a biasing signal that signifies that the determination has been made that the value of the monitored parameter has reached the applicable threshold, and there will be escalation. For example, when a logic device has been provided to make that determination, the first biasing mechanism can be configured to receive the biasing signal from that logic device. An example was described above for biasing signal BA from the device of FIG. 3.

The transitioning from the biased state to the unbiased state is also called biasing and deployment of the certain electrode. Deployment is for the certain electrode, and possibly also other electrodes of the system. It will be appreciated that deployment in this sense might not necessarily change much the position of the certain electrode with respect to the patient's body, but it will change the force with which it is pushed or biased towards the body.

The first biasing mechanism can be made in any way so as to cause pressure to be applied to the certain electrode against the support structure, and therefore bias the certain electrode towards the patient's body. Various embodiments of the first biasing mechanism include a spring that is released, causing the support structure to be tightened around the body, causing a balloon to be inflated, adding pressure to a hydraulic system, applying force such as with an electromagnet, and turning a screw gun arrangement so that turning result in a translation motion. The sample embodiment of FIG. 1 shows also a biasing mechanism 194.

A sample deployment is now described. FIG. 4A is a diagram according to an embodiment. A patient 482 is wearing a support structure 470, of which two portions are shown. Support structure 470 is made according to embodiments and, as with FIG. 1, it is shown only generically. A certain electrode 408 could be either a defibrillation electrode or an ECG electrode, and is coupled to support structure 470 in an unbiased state. In the instant of FIG. 4A, certain electrode 408 does not even contact the skin of patient 482. A biasing mechanism 494 is also coupled to support structure 470.

FIG. 4B is a diagram showing the same elements as FIG. 4A, except that biasing mechanism 494 exerts a biasing force 496 due to which certain electrode 408 is biased towards patient 482 against support structure 470. In the instant of FIG. 4B, certain electrode 408 contacts the skin of patient 482. Certain electrode 408 is less easily movable in FIG. 4B than in FIG. 4A.

In a number of embodiments the first biasing mechanism is preferably made so that it is further reversible, either by the wearer, or by a bystander, or by a remotely monitoring medical professional. Reversing would be upon verifying that there is no actionable episode to be addressed by the system, moves downwards in the scale of FIG. 2, and is the opposite of escalation. Reversing could be automatically enabled by further functionality. Or, reversing could be implemented by permitting the mechanically reverse motion of what deployed the certain electrode and any other electrodes. Care should be taken that reversing is not suggested prematurely, or by a person who does not understand the function of the system, such as a well-meaning but uninformed bystander.

It will be appreciated that, when the certain electrode is in the biased state, it can be counted on to make better electrical contact with the body. Accordingly, any ECG inputs received by the certain electrode preferably are trusted more when the certain electrode is in the biased state than in the unbiased state. Regardless, in a preferred embodiment, an additional, serendipitous check on the patient can be an ECG reading that is received incidentally while the certain electrode is in the unbiased state and whose content causes alarm. Such an ECG reading can be used in a number of ways, for tentative escalation. One example is for the biasing mechanism to cause the certain defibrillation electrode to transition to the biased state from the unbiased state responsive to an ECG reading of the patient that is received incidentally while the certain electrode is in the unbiased state.

In most embodiments, the certain electrode makes good electrical contact while biased, i.e. while the biasing mechanism exerts a biasing force. In some embodiments, however, the certain electrode includes adhesive material. The adhesive material can be always there, or be deployed right before the biasing. As the biasing mechanism causes the certain electrode to transition from the unbiased state to the biased state by exerting the biasing force, it in turn causes the certain electrode to adhere to the patient due to the adhesive material. The electrode can remain adhered even if the biasing mechanism discontinues exerting the biasing force.

Embodiments of the system of the invention may additionally include a memory. The memory can be configured to record various aspects, such as values of the parameter being monitored, an event of a threshold having been reached by the monitored parameter, an event of the certain electrode transitioning to the biased state form the unbiased state, and so on. In embodiments where the defibrillator of FIG. 3 is used, the memory can be memory 338.

Embodiments of the system of the invention may further include a user interface. The user interface can include output devices, such as a speaker, a display, a vibration mechanism etc., plus input devices such as a microphone, buttons, keys, and other implements that a user can activate or deactivate. The user interface can be configured to issue a query to the patient, to verify that they are conscious, and therefore confirm there is no cause for alarm from a detected value of the monitored parameter. Such can be, for example, when the patient's condition has reached or exceeded response-check threshold 220 of FIG. 2. In those instances, embodiments permit the wearer to enter an input in response to the query within a certain time, before the certain electrode transitions from the unbiased state to the biased state. An example is a "live man switch", which the wearer can push, to indicate they are fine. In such embodiments, the certain electrode can be configured to transition to the biased state only if a preset acceptable input has not been received in response to the query within a preset time after the query has been issued. In embodiments where the defibrillator of FIG. 3 is used, the user interface can be user interface 370.

If the option of querying the user is indeed provided, it can be further coupled with the advent of a serendipitous receipt of an ECG reading whose content causes alarm while the certain electrode is in the unbiased state. In such embodiments, the user query can be triggered as above.

As mentioned above, in some embodiments, the certain electrode is a defibrillation electrode. In these embodiments, the electrical charge stored in the capacitor of the system is configured to be delivered through the patient's body via the certain electrode, and also via another defibrillation electrode. In the particular example of FIG. 1, defibrillation electrode 108 is the certain electrode, and defibrillation electrode 104 is the other defibrillation electrode, while no separate ECG electrodes are provided. Certain electrode 108 can become deployed, as can electrode 104 by a suitable biasing mechanism.

Moreover, in other embodiments, the certain electrode can be an ECG electrode. In these embodiments, one or more ECG electrodes are thus provided above and beyond defibrillation electrodes. The one or more ECG electrodes can become deployed, as per the above.

When ECG electrodes are also provided, there are a number of options about the defibrillation electrodes. One option is for the defibrillation electrodes to be always attached to the patient by how they are coupled to the support structure. This is not very advantageous, however, as the intent is to liberate the patient from contact with electrodes for the long-term wear, so as to make compliance more palatable.

Another option is to have the defibrillation electrodes also be deployable. More particularly, the defibrillation electrodes can be coupled to the support structure. The coupling can be such that, while the support structure is worn by the patient, at least a particular or certain one of the defibrillation electrodes is either at an unbiased state or a biased state. Similarly with the above, when the particular defibrillation electrode is in the unbiased state, it is moveable with respect to the patient's body responsive to the patient's moving. Moreover, when the particular defibrillation electrode is in the biased state, the particular defibrillation electrode is biased towards the patient's body against the support structure so as to be less moveable with respect to the patient's body than when in the unbiased state.

When the defibrillation electrodes are also deployable, an ECG reading can advantageously be received also from the particular electrode that is deployed. Moreover, it is preferred to configure the electrical charge to be delivered through the patient's body when the particular defibrillation electrode is in the biased state, when defibrillation advised threshold 285 is exceeded. In fact, it is even more preferred to configure the electrical charge to be delivered through the patient's body only when the particular defibrillation electrode is in the biased state, to avoid wasting energy, or misdirecting the electrical charge.

When the defibrillation electrodes are also deployable, there are a number of embodiments. An embodiment is for at least one of the ECG electrodes to be attached to at least one of the defibrillation electrodes. As such, deploying the certain ECG electrode by the first biasing mechanism also deploys the defibrillation electrode. Attachment can be implemented in any number of ways. For example, the ECG electrode can be formed integrally with one of the defibrillation electrodes. In a preferred embodiment, the ECG electrode can be formed as a segmented electrode with a defibrillation electrode. In this option, the certain electrode can also be considered to be the defibrillation electrode, which has the further feature of one or more ECG electrodes attached to it.

Another embodiment is for at least one of the defibrillation electrodes to be truly distinct from the ECG electrodes. This option has the advantage that certain types of false alarm will result in deploying only the ECG electrodes upon partial escalation, but not the usually larger defibrillation electrodes. This option also has the disadvantage that two deployments may be needed, which requires more biasing structures in the system.

In such embodiments, a second biasing mechanism can be provided for the system, which is distinct from the first biasing mechanism. The second biasing mechanism can be configured to cause the certain or particular defibrillation electrode to transition from its unbiased state to its biased state.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on. This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described. These methods may also be practiced with additional operations, and by embodiments described above.

Some of these methods are for a defibrillator system that is wearable by a patient who may be moving, and which includes a support structure and electrodes coupled to the support structure. The electrodes are coupled such that, while the support structure is worn by the patient, at least a certain one of the electrodes is moveable with respect to the patient's body responsive to the patient's moving. The certain electrode can be a defibrillation electrode, an ECG electrode, or a combination of the two. Moreover, these flowcharts may find more detailed explanations in what is written elsewhere in this document.

Figure 5:
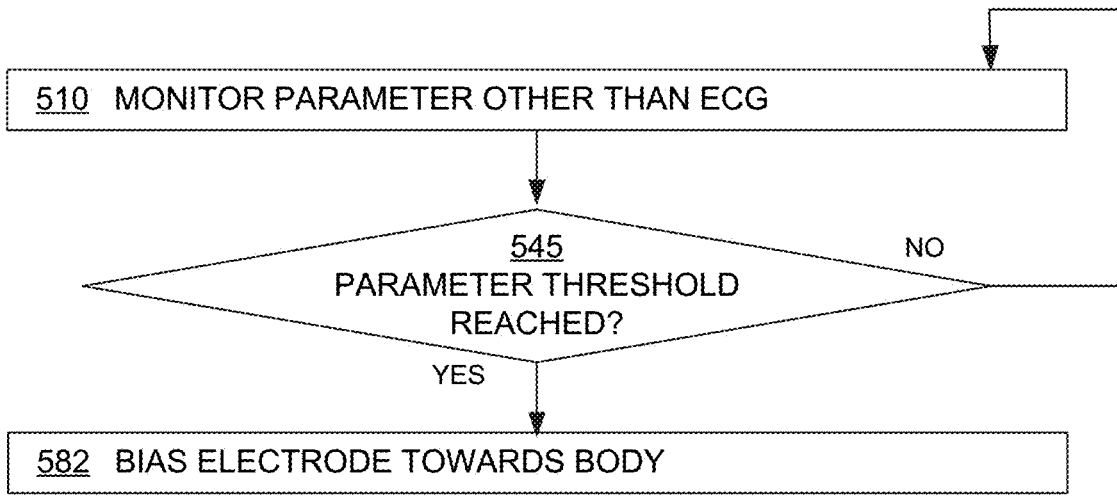
FIG. 5 is a flowchart for illustrating methods according to embodiments.

FIG. 5 shows a flowchart 500 for describing methods according to embodiments. According to an operation 510, at least one parameter of the patient is monitored, while the patient is wearing the support structure. The parameter is not an electrocardiogram ("ECG") of the patient. In some embodiments, the parameter is a motion of the patient's body. In other embodiments, the parameter is a physiological parameter, which could be one of the patient's blood perfusion, blood flow, blood pressure, blood oxygen level, pulsatile change in light transmission/reflection properties of perfused tissue, heart sounds and breathing sounds.

According to a next operation 545, it is determined whether a threshold has been reached for the monitored parameter. If not, execution returns to operation 510.

If yes, then according to a next operation 582, the certain electrode becomes biased towards the patient's body against the support structure. Accordingly, the certain electrode becomes less moveable with respect to the patient's body than previously. Biasing can be by exerting force, with implements such as described above.

Figure 6:
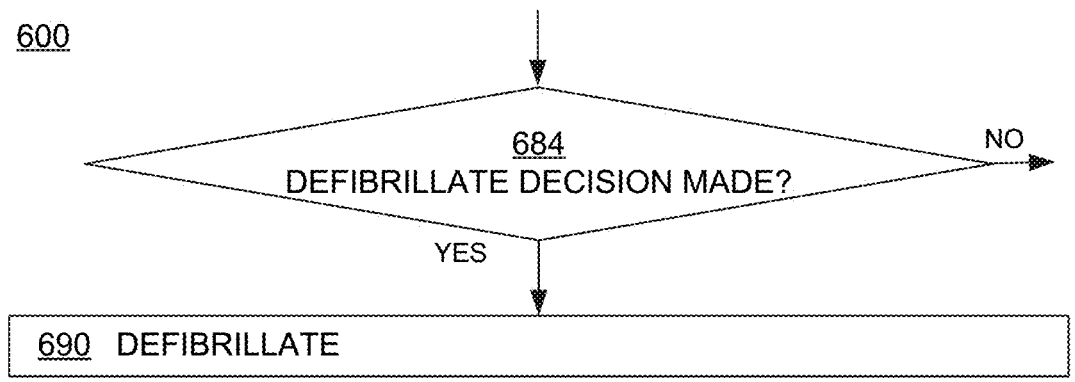
FIG. 6 is a flowchart segment for describing additional optional operations according to embodiments.

FIG. 6 shows a flowchart segment 600 for describing additional optional operations according to embodiments. The additional optional operations of flowchart segment 600 can be added to other flowcharts in this description.

According to an optional operation 684, it is inquired whether a defibrillate decision has been made. If not, execution can return to a previous operation. If yes, then according to a next operation 690, the patient is defibrillated.

Figures 7, 8:
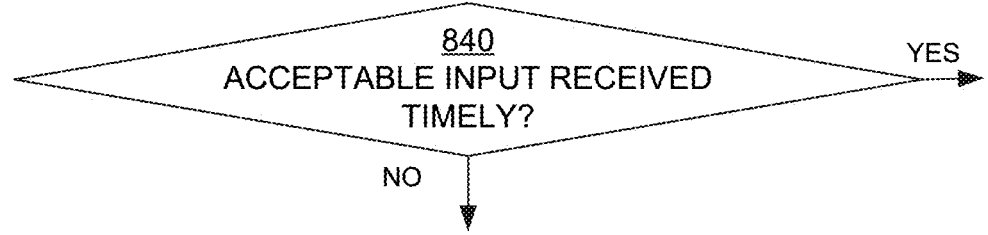
FIG. 7 is a flowchart segment for describing an additional optional operation according to embodiments.
FIG. 8 is a flowchart segment for describing additional optional operations according to embodiments.

FIG. 7 shows a flowchart segment 700 for describing additional optional operations according to embodiments. The additional optional operations of flowchart segment 700 can be added to other flowcharts in this description.

According to an optional next operation 747, an indication is recorded in a memory of an electrode becoming biased. This might have occurred, for example, per the previous operation 582 of FIG. 5.

FIG. 8 shows a flowchart segment 800 for describing additional optional operations according to embodiments. The additional optional operations of flowchart segment 800 can be added to other flowcharts in this description.

According to an optional operation 830, a query is issued to the patient. The query can be issued when a parameter has reached or exceeded response-check threshold 220 of FIG. 2.

According to a next operation 840, it is inquired whether a preset acceptable input in response to the query has been received timely, for example within a preset time after the query has been issued. If yes, then the patient can be presumed to not have had an SCA, and escalation of inquiry or perception of severity of their condition can be forestalled. If not, then further escalation is justified, and other measures can take place, such as biasing one or more electrodes, and so on.

Figure 9:
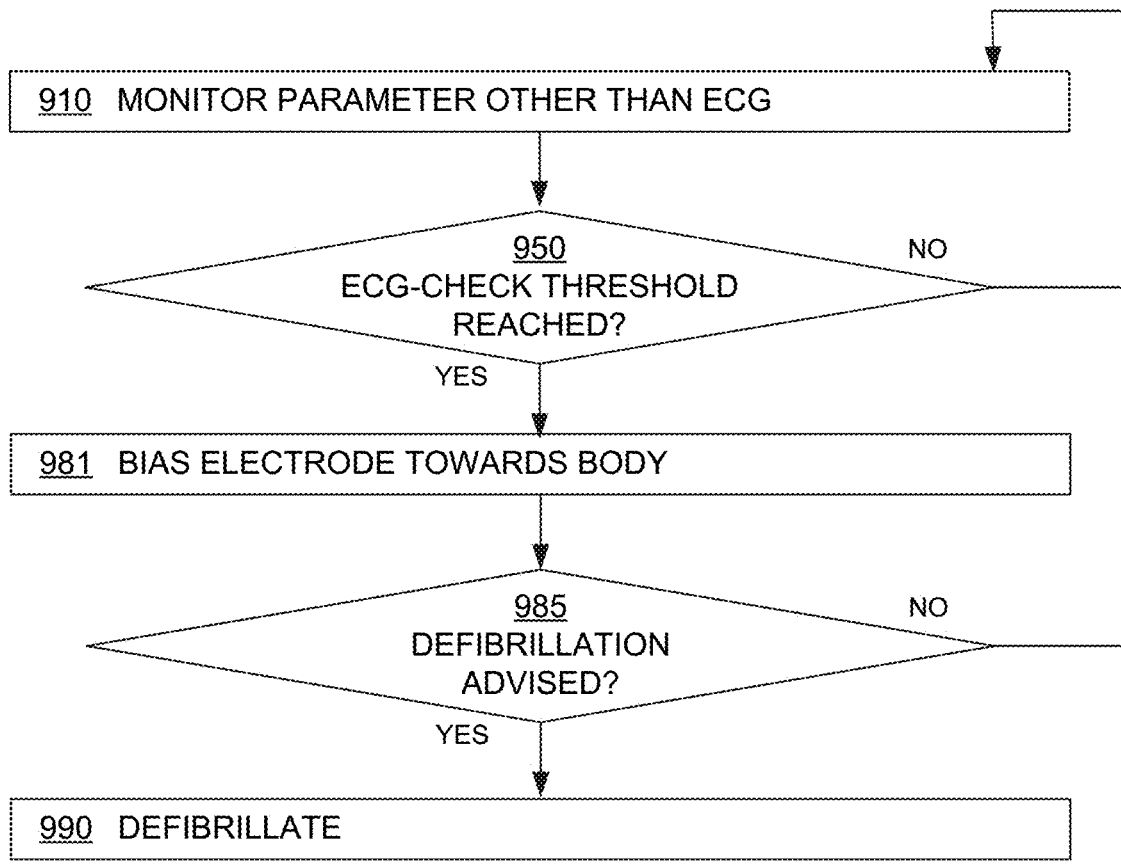
FIG. 9 is another flowchart for illustrating methods according to embodiments.

FIG. 9 shows a flowchart 900 for describing a method according to embodiments. According to an operation 910, a parameter is monitored that is not an ECG of the patient.

According to a next operation 950, it is determined whether an ECG-check threshold 250 has been reached for the parameter. If not, execution returns to operation 910.

If yes, then according to a next operation 981, the certain electrode becomes biased towards the patient's body against the support structure. As such, the certain electrode becomes less moveable with respect to the patient's body than previously.

According to a next operation 985, it is inquired whether defibrillation is advised. If not, execution can return to operation 910. If yes, then according to a next operation 990, the patient is defibrillated.

Figure 10:
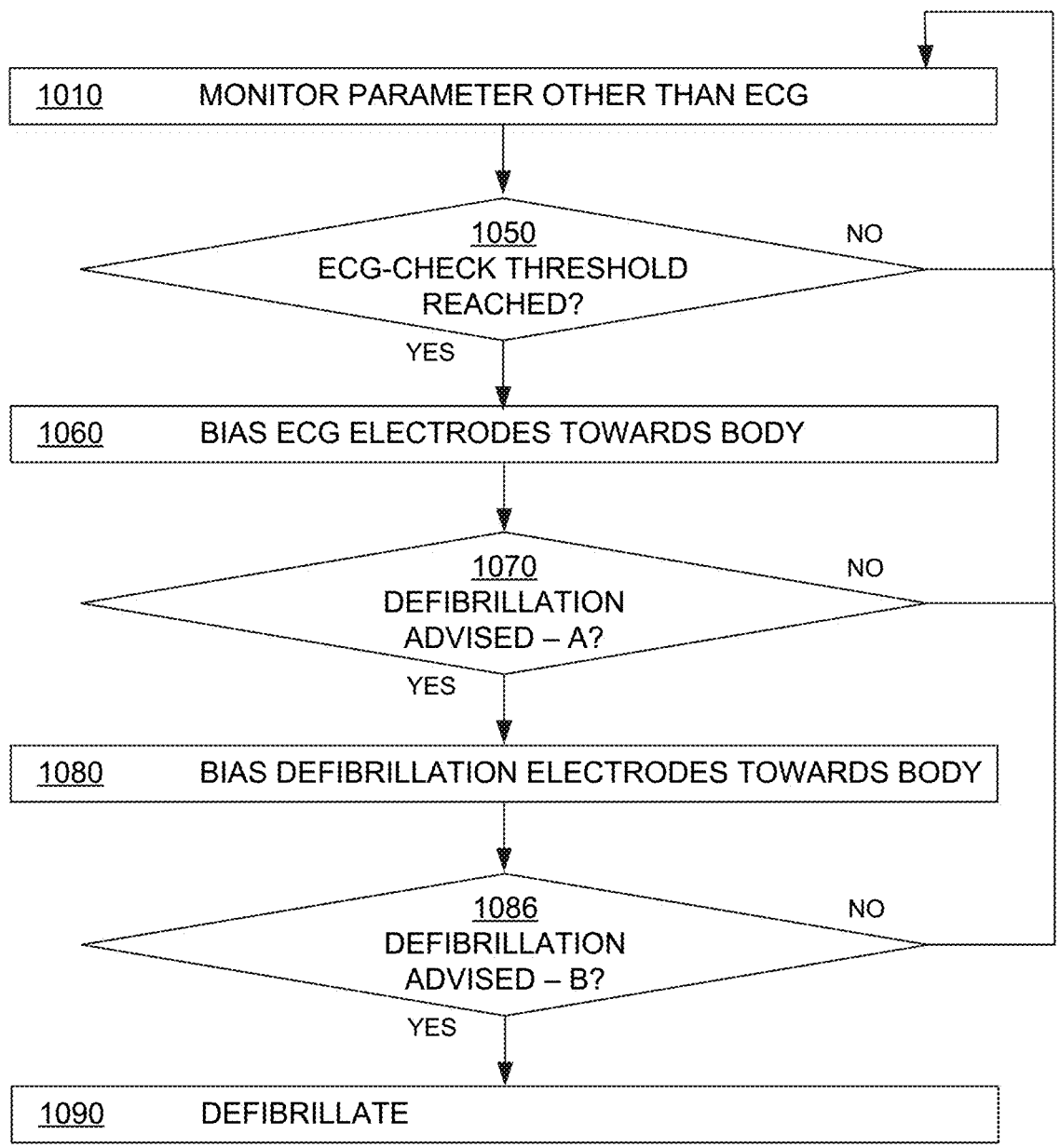
FIG. 10 is one more flowchart for illustrating methods according to embodiments.

FIG. 10 shows a flowchart 1000 for describing a method according to embodiments. Flowchart 1000 is for a device that has distinct ECG electrodes from defibrillation electrodes, with distinct respective biasing mechanisms. Unlike the usually large defibrillation electrodes, ECG electrodes maybe harder to aim to suitable locations on the patient's skin.

According to an operation 1010, a parameter is monitored that is not an ECG of the patient. According to a next operation 1050, it is determined whether an ECG-check threshold 250 has been reached for the parameter. If not, execution returns to operation 1010.

If yes, then according to a next operation 1060, the ECG electrodes become biased towards the patient's body against the support structure. As such, the ECG electrodes become less moveable with respect to the patient's body than previously.

According to a next operation 1070, it is first inquired whether defibrillation is likely advised. The first inquiry—also designated as "A" in the flowchart—of this operation 1070 is according to ECG readings received from the now biased ECG electrodes. The first inquiry of this operation 1070 can be more tentative than the upcoming inquiry. If not, execution can return to operation 1010.

If yes, then according to a next operation 1080, the defibrillation electrodes become biased towards the patient's body against the support structure.

According to a next operation 1086, it is again inquired whether defibrillation is advised. The second inquiry—also designated as "B" in the flowchart—of this operation 1086 is according to ECG readings received from the now biased defibrillation electrodes, and can be to determine whether threshold 285 has been reached or exceeded. If not, execution can return to operation 1010. If yes, then according to a next operation 1090, the patient is defibrillated.

Embodiments are capable of dealing with one or more signals from sensor modules. An example was seen in FIG. 1, where two sensor modules 121, 122 are shown. Other examples are now described, which rely on the above described elements, without repeating them.

Figure 11:
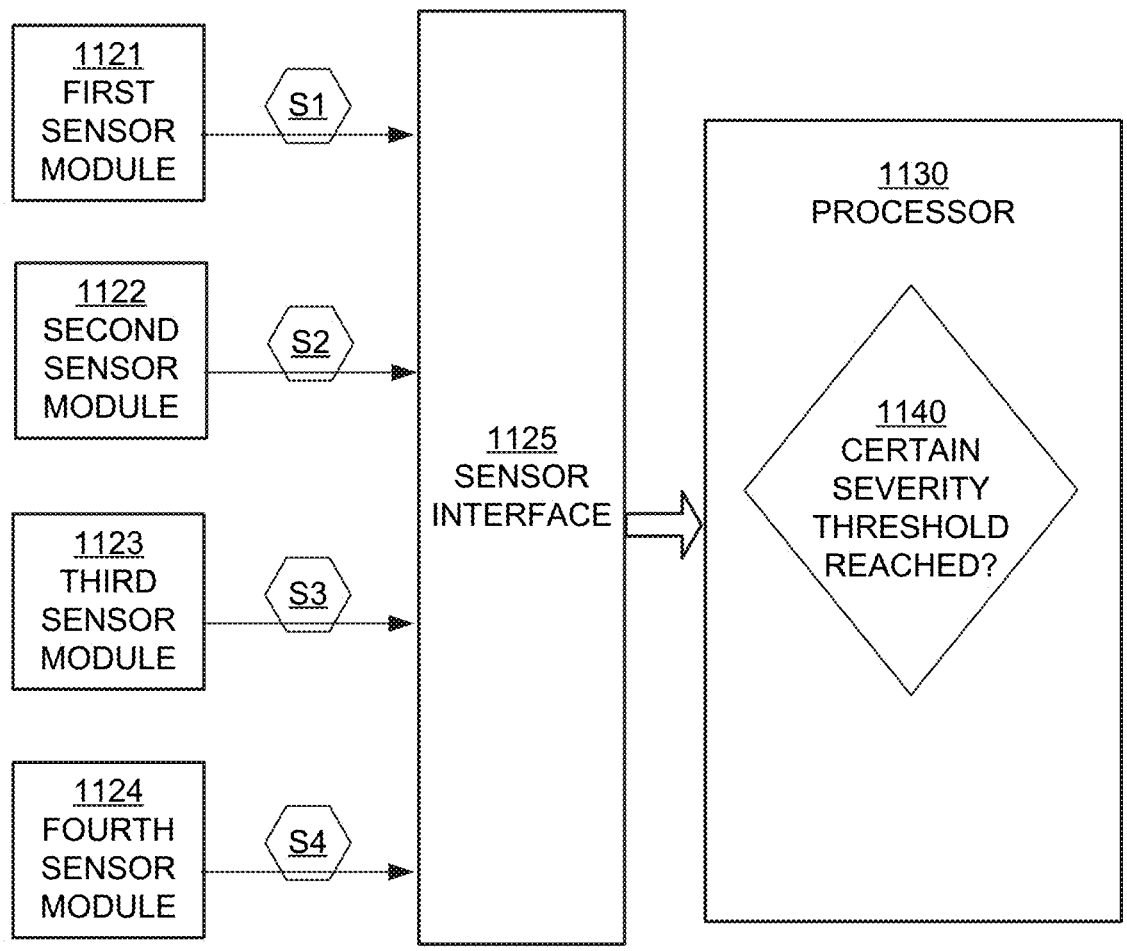
FIG. 11 is a diagram showing an example of how multiple different signals may be used to make a determination according to embodiments.

FIG. 11 shows four sensor modules 1121, 1122, 1123, 1124, which have respective names like "first", "second", etc. Of course, they can be characterized as first, second, etc. in any order. In embodiments, sensor modules 1121, 1122, 1123, 1124 are outside the defibrillator housing of the WCD system, such as sample housing 301 shown in FIG. 3.

Sensor modules 1121, 1122, 1123, 1124 may be configured to monitor respective parameters of the patient, such as a first parameter, a second parameter, etc. These parameters may be the same or different than each other. They may be the patient's ECG or not. In some embodiments, none of the parameters is the patient's ECG, so as to permit the patient to wear the support structure without having an electrode pressing against his body all the time. In some embodiments, the parameters are different from each other, given what is convenient to wear at the time, and where on the body it would have to be applied.

Depending on their construction and the parameter they monitor, sensor modules 1121, 1122, 1123, 1124 may be placed at a suitable location with respect to the patient's body. Different locations may be convenient depending on the time of day, and what the patient is doing at the time. Accordingly, embodiments provide versatility, which permits flexibility for using the entire WCD system.

Sensor modules 1121, 1122, 1123, 1124 may be further configured to make available respective signals S1, S2, S3, S4 that are generated from the respective parameters they monitor. So, first sensor module 1121 may make available first signal 51 generated from the first parameter, second sensor 1122 module may make available a second signal S2 generated from the second parameter, and so on.

The sensor modules may be implemented in a number of ways. In some embodiments, one or more of sensor modules 1121, 1122, 1123, 1124 may be specific to the WCD system, and in fact be part of the WCD system. In other embodiments, one or more of sensor modules 1121, 1122, 1123, 1124 may be implemented by commercially available devices that are wearable, such as watches, and portable, such as smartphones. Such devices may be general-purpose, and be made usable by the WCD system by having a custom software application loaded thereon. Further, in view of this description, it will be recognized that a software application can be written that can convert a general-purpose commercially available electronic device into a sensor module usable by a WCD system according to embodiments. In addition, such devices can be disguised to appear like bracelets, wristbands, necklaces, or concealed, by being wrapped around an ankle. Examples are now described.

Figure 12:
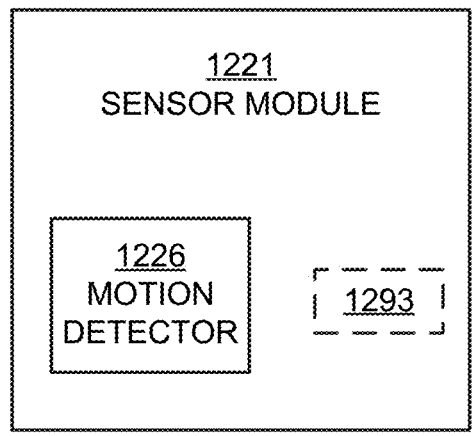
FIG. 12 is a block diagram of a sample sensor module made according to embodiments.

In some embodiments, one or more of sensor modules 1121, 1122, 1123, 1124 include a motion detector, and the parameter they monitor is a motion of the patient's body. For example, as seen in FIG. 12, a sensor module 1221 includes a motion detector 1226. The signal made available by sensor module 1221 can be indicative of the motion of sensor module 1221, and thus of the patient's body. A motion detector for different ranges of motion may be implemented by GPS that informs of the location, and thus the rate of change of location over time. Of course, sensor module 1221 may include additional components for making its signal available, communicating it, and so on. For example, it may include a communication device 1293, which is described later in this document.

Figure 13:
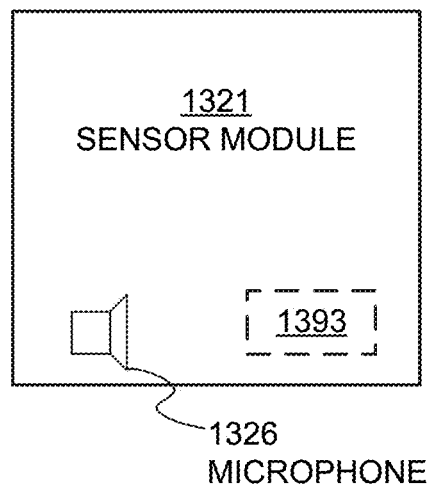
FIG. 13 is a block diagram of a sample sensor module made according to embodiments.

In some embodiments, one or more of sensor modules 1121, 1122, 1123, 1124 include a microphone, and the parameter they monitor can be a sound like heart sounds, a heart rate of the patient from its sound, a breathing sound of the patient, and so on. For example, as seen in FIG. 13, a sensor module 1321 includes a microphone 1326. Sensor module 1321 may work better while the patient is sleeping at night, during which time the typically sensed sounds can be more easily characterized. Again, sensor module 1321 may also include a communication device 1393 and other components.

Alternatively, the sensor module could include ultrasound by a module worn on the chest, to detect heart wall motion consistent with reasonable cardiac coordination and function. Or, the sensor module could include a Doppler device for detecting blood flow.

Figure 14:
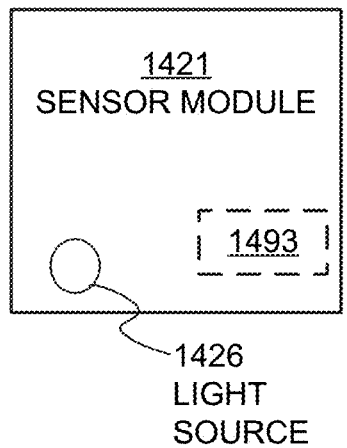
FIG. 14 is a block diagram of a sample sensor module made according to embodiments.

In some embodiments, one or more of sensor modules 1121, 1122, 1123, 1124 includes a light source. For example, as seen in FIG. 14, a sensor module 1421 includes a light source 1426. Sensor module 1421 may also include a communication device 1493 and other components. A parameter monitored by sensor module 1421 can be a pulsatile blood flow of the patient, a blood perfusion of the patient, a blood pressure of the patient, a blood oxygen level of the patient, or change in light transmission or reflection properties of perfused tissue of the patient. Accordingly, sensor module 1421 could include a pulse oximeter, a cuff, etc. Pulsatile blood flow can be detected by an optical detector of worn on a finger, wrist, ankle, headband, or in ear (embedded in a hearing aid, or in an expanding ear-plug sort of thing). Any of these modules with optical sensing could be either emitting light into tissue and sensing variations of reflected or transmitted light, or possibly looking for oscillations in ambient light reflected or transmitted by tissue.

In addition, pulse detection is taught at least in Physio-Control's U.S. Pat. No. 8,135,462, which is hereby incorporated by reference in its entirety. In addition, a person skilled in the art may implement other ways of performing pulse detection.

In some embodiments, one or more of sensor modules 1121, 1122, 1123, 1124 includes a light source, and is configured to detect a color of a skin of the patient. This may be particularly useful, because the skin of a white person may become ashen-colored if the blood stops circulating, such as during an SCA. An example is now described.

Figure 15:
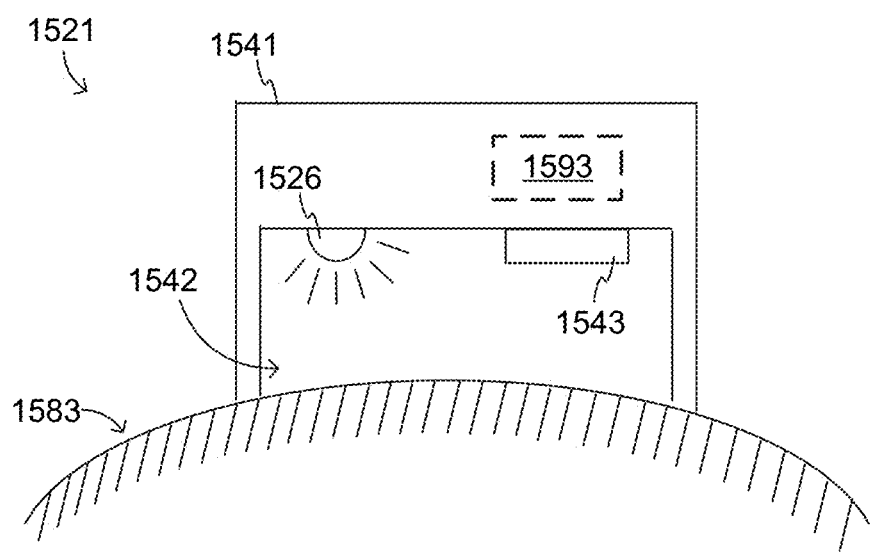
FIG. 15 is a diagram of a sample sensor module made according to embodiments.

FIG. 15 is a diagram of a sensor module 1521 made according to embodiments, which has been placed on skin 1583 of a patient. Sensor module 1521 has a housing 1541 that is held against skin 1583, such as by being attached thereon by tape or an elastic band, neither of which is shown. It should be noted, however, that this attaching is not as uncomfortable as having an electrode attached, because it need not involve chemicals, and actually only a small portion of the covered surface of skin 1583 is actually contacted. In fact, sensor module 1521 may define a cavity 1542, and only the rim of cavity 1542 contacts skin 1583. Sensor module 1521 may also have a light source 1526 that illuminates cavity 1542, and thus also illuminates the portion of skin 1583 surrounded by the rim of cavity 1542. Sensor module 1521 may further have a small imager 1543 for imaging the illuminated skin portion, for purposes of detecting its color. Imager 1543 can be made by a few pixels or one or more photodetectors. If or when the skin of a white patient turns ashen color, it is bound to reflect less white light than previously. Sensor module 1521 may also include a communication device 1593 and other components.

In some embodiments, one or more of sensor modules 1121, 1122, 1123, 1124 includes an elastic band that is configured to be placed so as to be part of a loop around a chest of the patient. An example is now described.

Figure 16A:
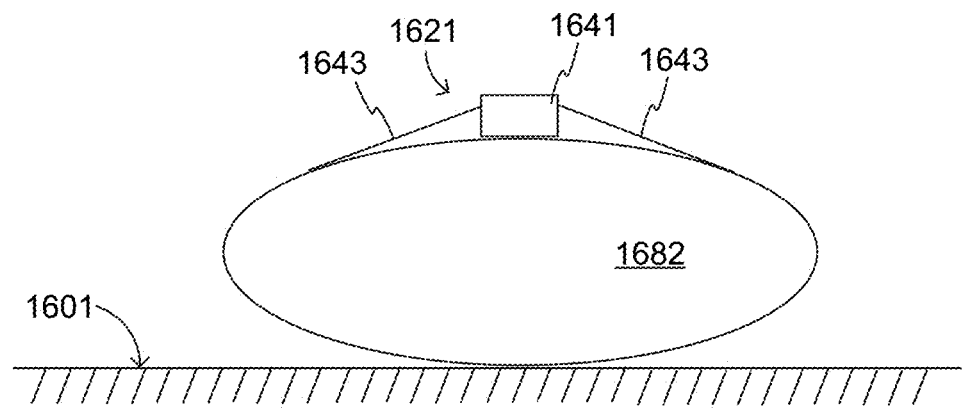
FIG. 16A is a diagram of a sample sensor module made according to embodiments, being used by a patient who is sleeping.

FIG. 16A is a diagram of a sensor module 1621 made according to embodiments, which is being used by a patient 1682 who is sleeping on a surface 1601. A section view of the torso of patient 1682 is shown. Sensor module 1621 has a housing 1641 that is held against the torso by an elastic band 1643. Elastic band 1643 may be long enough to form an entire loop be around the chest of patient 1682. Alternately, a remainder of the loop may be formed by one or more other members, which may be elastic or not. The patient's breathing thus may stretch and release the band. This stretching and releasing may be detected in a number of ways, and an example is now described.

Figure 16B:
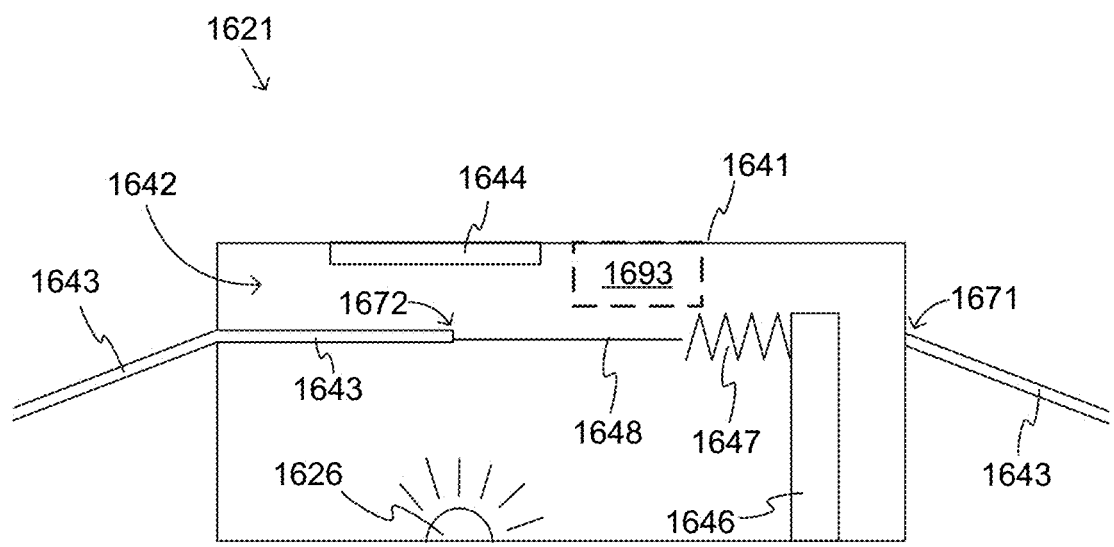
FIG. 16B is a diagram of a detail of a sample embodiment of the sensor module of FIG. 16A.

FIG. 16B is a diagram of a detail of a sample embodiment of the sensor module of FIG. 16A. In this example, elastic band 1643 has two ends 1671, 1672 attached to housing 1641, and housing 1641 is thus pressed on the chest of patient 1682 by the stretching of elastic band 1643. Housing 1641 has a cavity 1642, and end 1672 reaches within housing 1641. In addition, the sensor module also includes a spring 1647 that is coupled to end 1672, for example via a thread 1648. Accordingly, spring 1647 keeps band 1643 stretched against a fixed post 1646. The patient's breathing causes end 1672 to oscillate from left to right and back again.

The oscillation of end 1672 can be detected in a number of ways. In the example of FIG. 16B, a light source 1626 can project light that can be imaged by imager 1644. Imager 1644 can be a pixel array, a small linear array of larger photodetectors, and so on. It helps if band 1643 is wide and maintained wide at end 1672, while thread 1648 is thin, so that end 1672 will cast a shadow, helping imager 1644 detect better. If higher detection sensitivity is desired, end 1672 may be moved closer to light source 1626 than is suggested by the diagram, so that the left-ward move caused by an inhalation of the patient will remove more shadow from imager 1644. Sensor module 1621 may also include a communication device 1693 and other components. A drawback in detecting breathing is that breathing can continue at least briefly after the beginning of cardiac arrest.

In many embodiments, at the time of fitting a WCD system to a patient, it is preferred to have a process for determining which of various modules to use, and/or a calibration procedure for them that is specific to the patient. For example, a patient who normally breathes heavily may do well with the sensor module of FIG. 16A, a patient who is white may do well with the sensor module of FIG. 15, and so on.

In yet other embodiments, both the patient's physiological parameter and motion can be monitored in combination. The value of the physiological parameter becomes better informed from the motion profile, as is the appropriate threshold for determining whether an actionable episode is taking place so as to escalate. Thresholds, such as threshold 220, can be adjusted accordingly. For example, if the patient is running then a somewhat higher pulse rate may be tolerated until a time after they stop, without needing to escalate, and so on.

In some embodiments, one or more of the sensor modules include communication devices, such as communication devices 1293, 1393, 1493, 1593 and 1693. These devices can be configured to communicate the signal that is made available by their sensor module, and may be implemented in a number of ways.

In some embodiments these communication devices are configured to communicate the first signal substantially periodically, from their own initiative. In some embodiments these communication devices are configured to receive a polling signal, and to communicate their signal responsive to receiving the polling signal. The polling signal can be an interrogation signal from another component of the WCD system, such as a sensor interface. When responding to a polling signal, they can again measure the stored parameter, or respond with a previously measured and stored value. Or, they can permit the polling signal to extract the signal that they make available, for example in the form of a stored value. In addition, if there are criteria for a sensor module to doubt the validity of its own measurement, the signal itself may communicate this doubt, or the signal might not be made available, as described later in this document.

In some embodiments these communication devices operate in a wired sense, in that the signal is communicated via a wire. In other embodiments these communication devices operate wirelessly, for example using Bluetooth, RFID, etc., each time with appropriate pairing to ensure the integrity of the communication of the signal. The RFID implementation may be with the sensor module writing to its own RFID tag the value of the time, and permit the sensor interface to use an RFID reader to query the RFID tag.

In some embodiments, some of the sensor modules are used at some times, while others of the sensor modules are used at other times. Provisions can be made, then, so that the sensor modules do not contribute signals to the WCD system while they are not being used. These provisions may be useful in the event that wirelessly operating sensor modules may be nearby while they are not used at the time, for example being recharged at night while the patient is sleeping. There are a number of ways of making such provisions for the sensor modules, for example by equipping them with ON/OFF switches, status sensors, ensuring they do not make available their signal while they are being recharged, and so on. According to embodiments, there can be further provisions for a patient to confirm that the signals from the appropriate sensors are being made available and/or being transmitted. For example, one of the sensor modules may include an active visual indicator that is configured to indicate when its signal is being made available and/or being transmitted. Additional examples are now described.

Figure 17A:
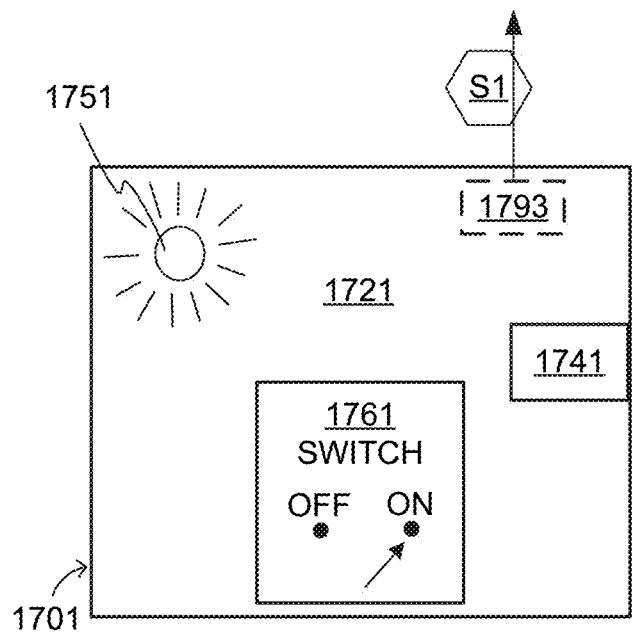
FIGS. 17A and 17B are differential drawings showing how a sensor module made according to embodiments can stop making its signal available and/or communicating it, when it is turned off.
Figure 17B:
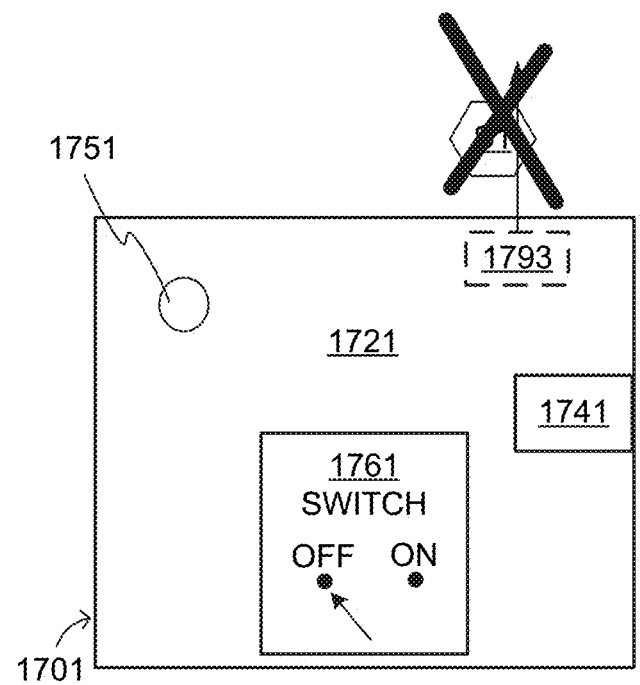

FIGS. 17A and 17B are differential drawings showing how a sensor module made according to embodiments can stop making its signal available and/or communicating it, when it is turned off. These two drawings can be characterized as differential because they show a single sensor module 1721 in different states, to facilitate comparison based on their similarities and differences.

In particular, FIG. 17A shows a sensor module 1721 that includes a housing 1701. Housing 1701 is configured to be coupled to the patient's body, which is not shown. Sensor module 1721 also includes a sensor 1741 coupled to housing 1701. Sensor 1741 can be configured to monitor a parameter of the patient, while housing 1701 is coupled to the patient's body. Given what the parameter is, it will be easy to determine a good position of the patient's body to couple to. Given the position of the body, it will be easy to determine how to couple to the body, e.g. with a strap, around a finger, as shown previously, etc. Sensor module 1721 may thus make available a signal 51 that is generated from the monitored parameter. Sensor module 1721 further may include a communication device 1793 configured to communicate signal S1. Sensor module 1721 additionally may include an active visual indicator 1751 that is configured to indicate whether or not signal S1 is being made available, or whether or not signal S1 is being communicated, as the case may be.

Sensor module 1721 further includes a switch 1761. Switch 1761 can be configured to place sensor module 1721 in an ON state or an OFF state. The OFF state can be a state where power is turned off, or a state of low-power dormancy ("sleep"). In this example, switch 1761 is shown as an ON/OFF switch. Switch 1761 can be manual, and accessed externally by the patient, as the patient is managing which sensor module to use at the time. Switch 1761 can alternately be implemented internally as an electronic state machine, a software flag, and thus be set in the ON state or in the OFF state by another component of the WCD system. For example, in some embodiments, sensor module 1721 may be intentionally lightly bumped against the sensor interface as a way of being wirelessly paired with it, and thus being turned ON from a dormant OFF state. Unpairing may be by double-bumping, etc.

In FIG. 17A, switch 1761 indicates that sensor module 1721 is in the ON state. Signal S1 is being made available, and communicated. Active visual indicator 1751 is shown as lit, to give confidence to the patient that sensor module 1721 is ON, and signal S1 is being made available. If communication device 1793 is indeed provided, active visual indicator 1751 can be configured to indicate that signal S1 is being further communicated.

In such embodiments, sensor module 1721 can be configured to not make available its signal S1, if sensor module 1721 is in the OFF state. For example, as seen in FIG. 17B, switch 1761 is in the OFF position, and signal S1 is either not being made available, or not communicated or both. Active visual indicator 1751 is accordingly shown as not lit.

In some of the embodiments of FIGS. 17A and 17B, switch 1761 is manual. This may introduce error, if the switch is set manually by the patient moving around, the WCD system bumping into the environment, etc. This source of error may be ameliorated by protective cover over switch manual 1761.

In some of the embodiments of FIGS. 17A and 17B, the patient would have to set switch 1761 manually. This may introduce error, if the patient forgets the instructions, forgets to reset the switch upon taking off sensor module 1721—etc. In some embodiments, less such participation by the patient is desired. Additional examples are now described, where the sensor module may detect by itself how it is being used, and control its signal accordingly.

Figure 18A:
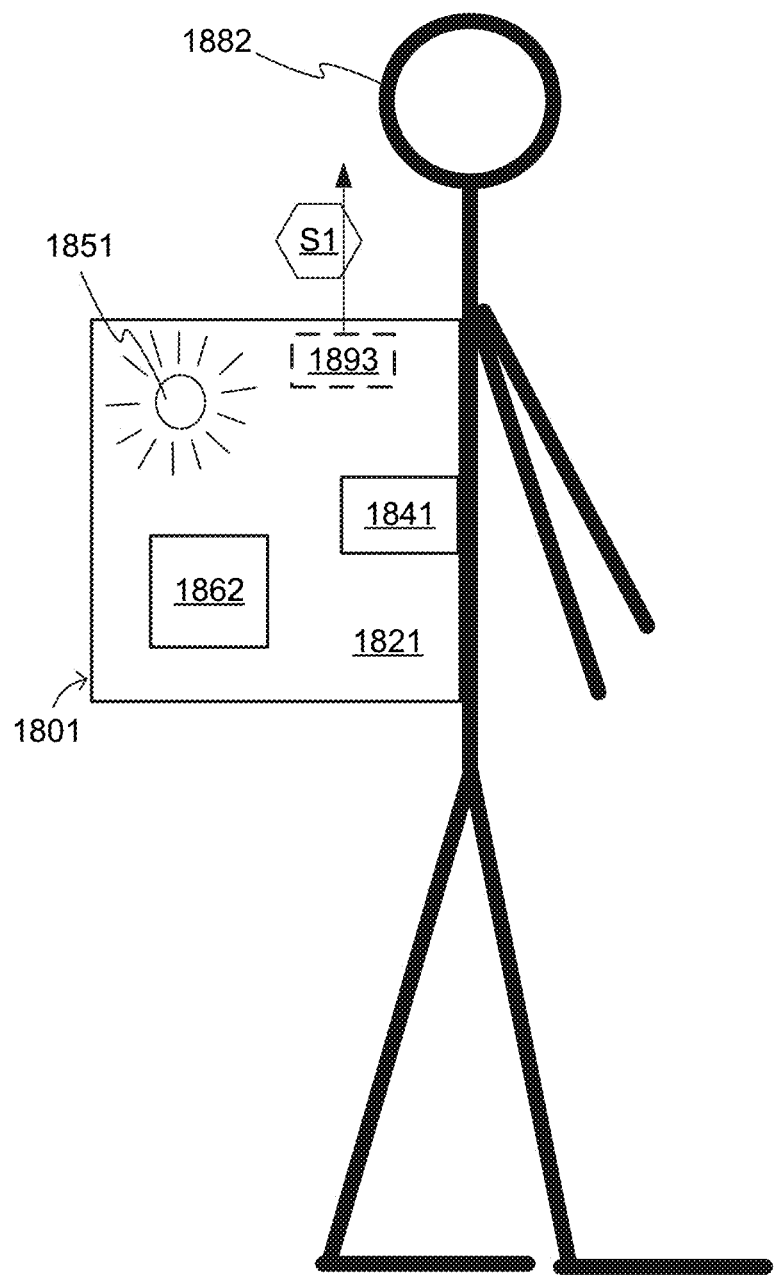
FIGS. 18A and 18B are differential drawings showing how a sensor module made according to embodiments can stop making its signal available and/or communicating it, when it detects that it is no longer monitoring the patient.
Figure 18B:
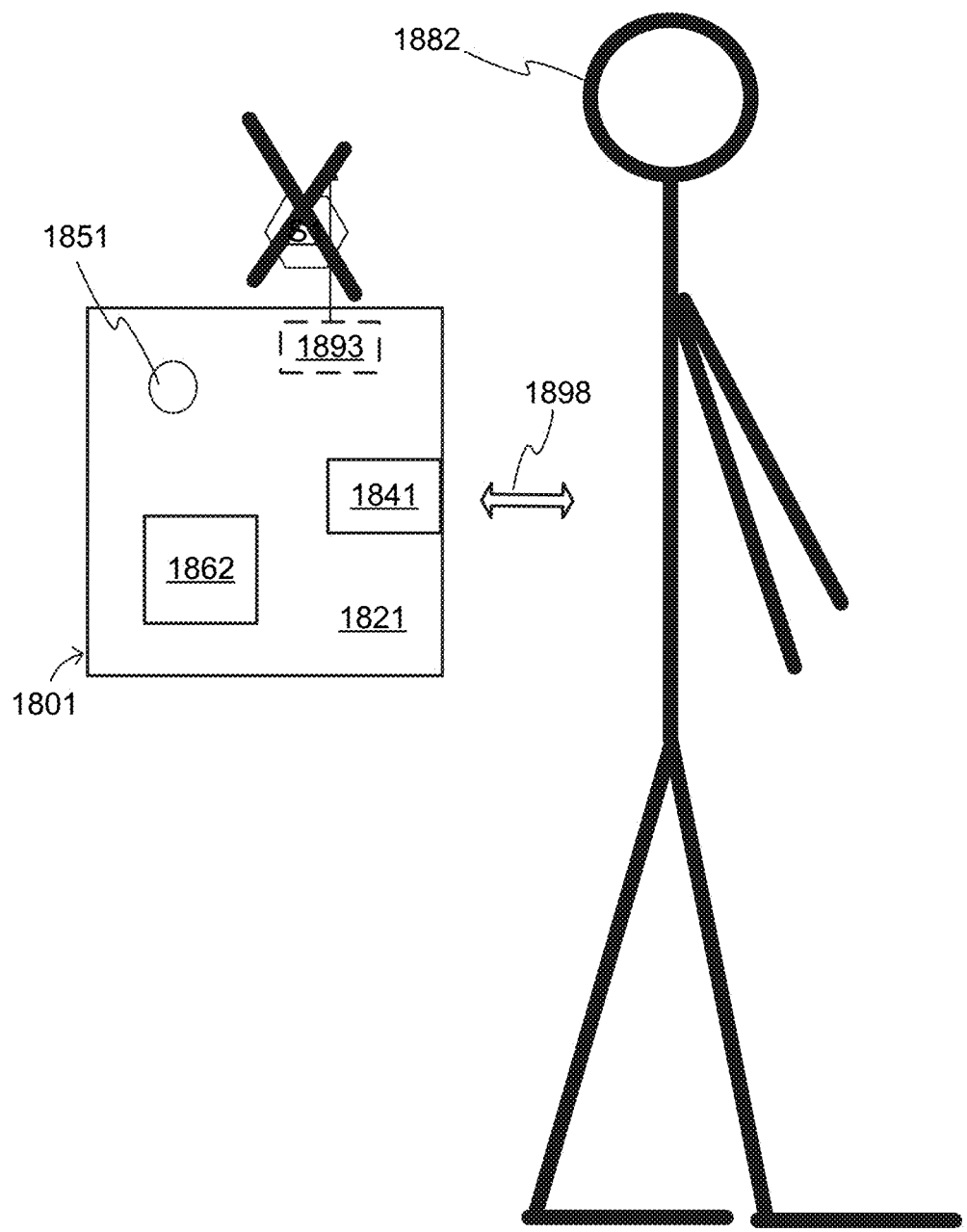

FIGS. 18A and 18B are differential drawings showing how a sensor module made according to embodiments can stop making its signal available and/or communicating it, when it detects that it is no longer monitoring the patient.

In particular, FIG. 18A shows a sensor module 1821 that includes a housing 1801. Housing 1801 is configured to be coupled to a patient's body, and is indeed so coupled to the body of a patient 1882. Sensor module 1821 also includes a sensor 1841 coupled to housing 1801. Sensor 1841 can be configured to monitor a parameter of patient 1882, while housing 1801 is coupled to the body of patient 1882. Sensor module 1821 may thus make available a signal S1 that is generated from the monitored parameter. Sensor module 1821 further may include a communication device 1893 configured to communicate signal S1. Sensor module 1821 additionally may include an active visual indicator 1851 that is configured to indicate that signal S1 is being made available, or that signal S1 is being communicated, as the case may be.

Sensor module 1821 further includes a status sensor 1862. Status sensor 1862 can be configured to determine whether the monitored parameter meets a validity criterion. The validity criterion can be about the parameter that is monitored, whether any measurements are valid or not. It is understood that the determination might not always be the correct one, but only an inference.

The status sensor may be implemented in hardware, software, or combination thereof, and operate in a number of ways. For example, the validity criterion might not be met depending on whether or not the values of the parameter monitored by sensor 1841 are consistent with values expected for the patient a) doing well, b) experiencing an SCA, or c) wearing or no longer wearing the sensor module.

In embodiments, status sensor 1862 may use patient status data additional to or different from what is learned by sensor 1841 monitoring the patient parameter. In such embodiments, status sensor 1862 may include one or more of a temperature sensor, a time-keeping mechanism, a motion sensor, a light sensor, a capacitance sensor, etc.

The temperature sensor may exploit the fact that the patient's temperature is normally within a narrow range. It can exploit this by being placed close to the patient's skin, and relatively shielded from the surroundings. Then, if the temperature changes to a different level, such as room temperature, then sensor module 1821 may have been removed from the patient's body.

The time-keeping mechanism may track the time of day, and create expectations as to what other patient status data might be, such as motion and ambient light. In turn, such patient status data might be checked against an output of a motion sensor and a light sensor that tracks an amount of ambient light. A capacitance sensor may help detect well any sudden changes in capacitance, such as might happen when sensor module 1821 is being taken on or taken off. All this data can help improve the determination of whether the patient is wearing or no longer wearing the sensor module and, if wearing it, whether the patient is doing well or not.

In FIG. 18A, sensor module 1821 is coupled to the body of patient 1882, by virtue of housing 1801 being coupled to the body of a patient 1882. Signal S1 is being made available, and communicated. Active visual indicator 1851, which could be an LED, is shown as lit. This may give confidence to the patient that sensor module 1821 is ON, and signal S1 is being made available. If communication device 1893 is indeed provided, active visual indicator 1851 can be configured to indicate that signal S1 is being further communicated.

In such embodiments, sensor module 1821 can be configured to not make available its signal S1, if it is determined that the first parameter does not meet the validity criterion. For example, as seen in FIG. 18B, there is a physical separation 1898 between patient 1882 and sensor module 1821. In other words, sensor module 1821 is no longer coupled to the body of patient 1882—patient 1882 has removed sensor module 1821. The validity criterion is determined to not be met. Accordingly, signal S1 is either not being made available, or not communicated or both. Active visual indicator 1851 is accordingly shown as not lit.

Figure 19A:
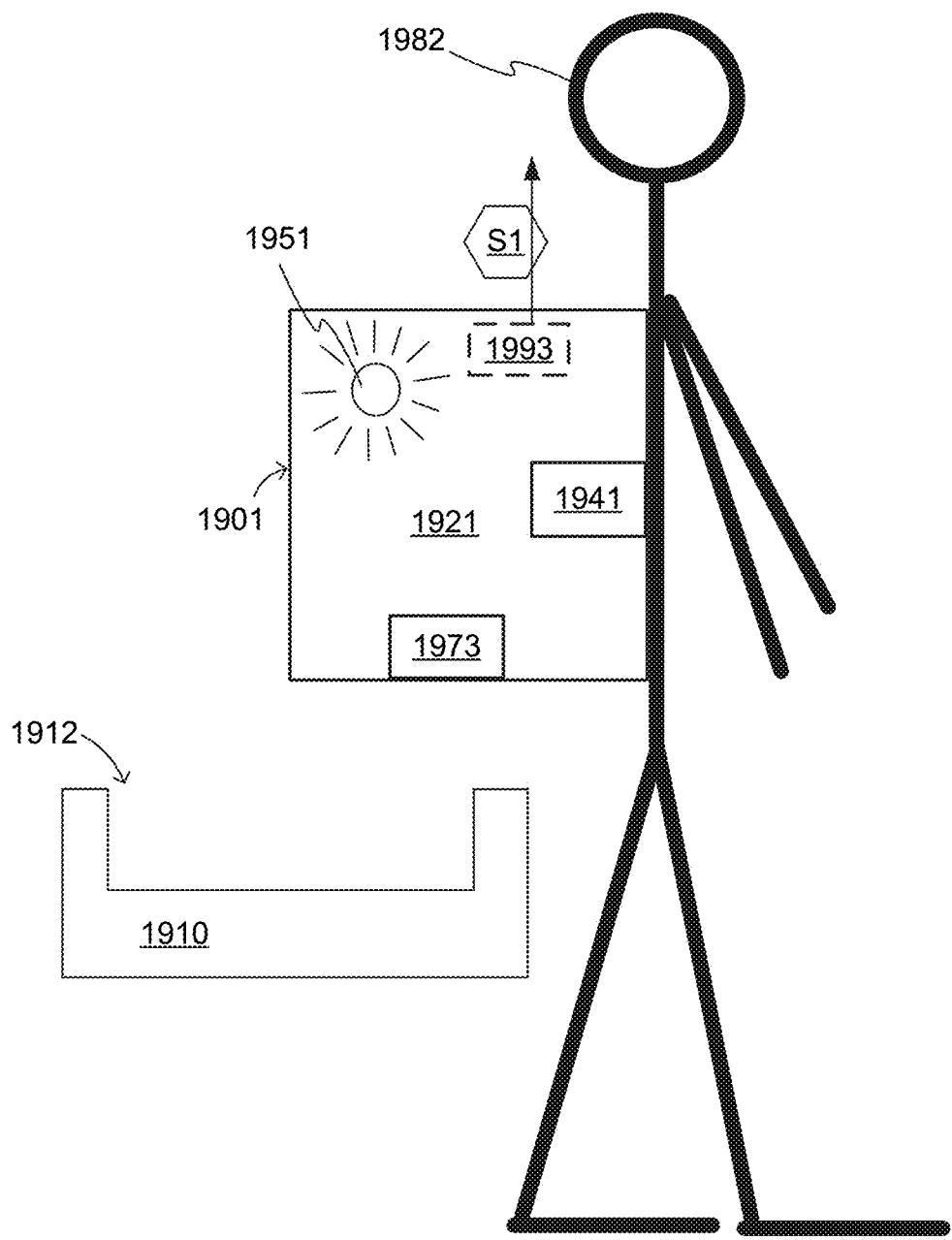
FIGS. 19A and 19B are differential drawings showing how a sensor module made according to embodiments can stop making its signal available and/or communicating it, while being charged.
Figure 19B:
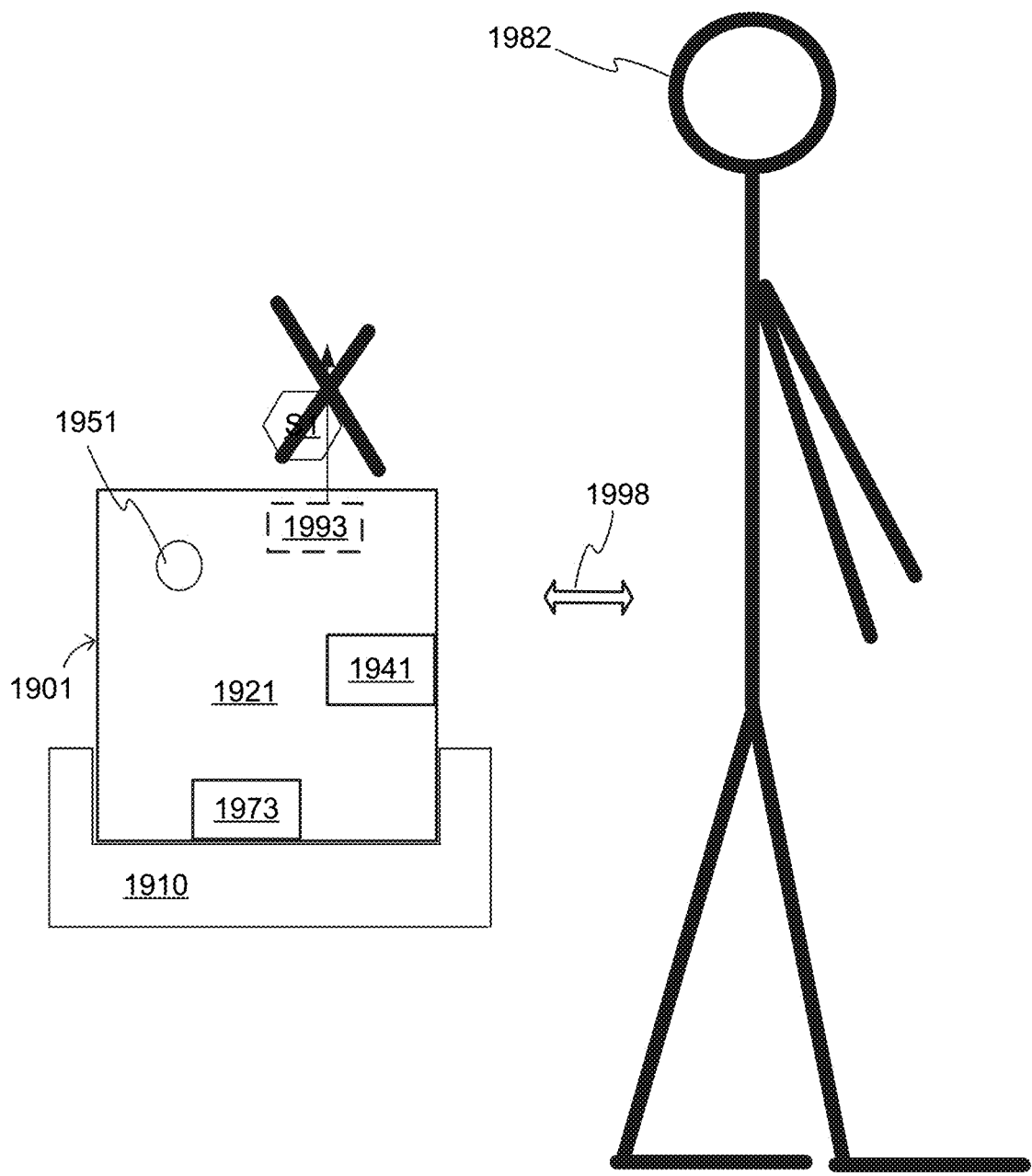

FIGS. 19A and 19B are differential drawings showing how a sensor module made according to embodiments can stop making its signal available and/or communicating it, while being charged. The inference is that, while being charged, the sensor module necessarily is not monitoring the patient.

In particular, FIG. 19A shows a sensor module 1921 that includes a housing 1901. Housing 1901 is configured to be coupled to a patient's body, and is indeed so coupled to the body of a patient 1982. Sensor module 1921 also includes a sensor 1941 coupled to housing 1901. Sensor 1941 can be configured to monitor a parameter of patient 1982, while housing 1901 is coupled to the body of patient 1982. Sensor module 1921 may thus make available a signal S1 that is generated from the monitored parameter. Sensor module 1921 further may include a communication device 1993 configured to communicate signal S1. Sensor module 1921 additionally may include an active visual indicator 1951 that is configured to indicate that signal S1 is being made available, or that signal S1 is being communicated, as the case may be.

In FIG. 19A, sensor module 1921 is coupled to the body of patient 1982, by virtue of housing 1901 being coupled to the body of a patient 1982. Signal S1 is being made available, and communicated. Active visual indicator 1951 is shown as lit, to give confidence to the patient that sensor module 1921 is ON, and signal S1 is being made available. If communication device 1993 is indeed provided, active visual indicator 1951 can be configured to indicate that signal S1 is being further communicated.

Sensor module 1921 further includes a rechargeable battery 1973 within housing 1901. Rechargeable battery 1973 can be configured to be charged. Charging can happen via a charging station 1910, which may have a receptacle 1912. Charging station 1910 may or may not be part of the WCD system. Rechargeable battery 1973 can be configured to be charged while housing 1901 is placed in receptacle 1912 of charging station 1910. A charging visual indicator (not shown) on sensor module 1921 can be configured to indicate that rechargeable battery 1973 is indeed being charged, while housing 1901 is placed in charging station 1910.

In such embodiments, sensor module 1921 can be configured to not make available its signal S1, while the first housing is placed in the charging station. For example, as seen in FIG. 19B, there is a physical separation 1998 between patient 1982 and sensor module 1921. In other words, sensor module 1921 is no longer coupled to the body of patient 1982, because sensor module 1921 is being charged. Accordingly, signal S1 is either not being made available, or not communicated or both. Active visual indicator 1951 is accordingly shown as not lit.

In some embodiments, the signal by a sensor module encodes a value of the parameter monitored by the module. A decision, then, as to whether the value should create an alarm, or whether a severity threshold is reached or exceeded, is made by the component of the WCD system receiving the signal.

In some embodiments, the signal by a sensor module encodes an alarm generated from a value of the first parameter. In other words, the sensor module itself makes a determination of whether the monitored first parameter has a value that causes alarm, and the signal is the alarm. For example, a detection that blood flow is suddenly discontinued could generate such an alarm.

In some embodiments, a WCD system also includes a sensor interface. The sensor interface can be coupled to the defibrillator housing, although there are other options. Sample sensor interfaces 325, 1125 are shown in FIGS. 3 and 11 respectively.

The sensor interface can be configured to receive one or more of the signals that are made available, and/or communicated by the sensor modules. In the example of FIG. 11, sensor interface 1125 is configured to receive all four signals S1, S2, S3, S4. The signals may be received by the sensor interface wirelessly, or via one or more wires. Examples are now described.

Figure 20:
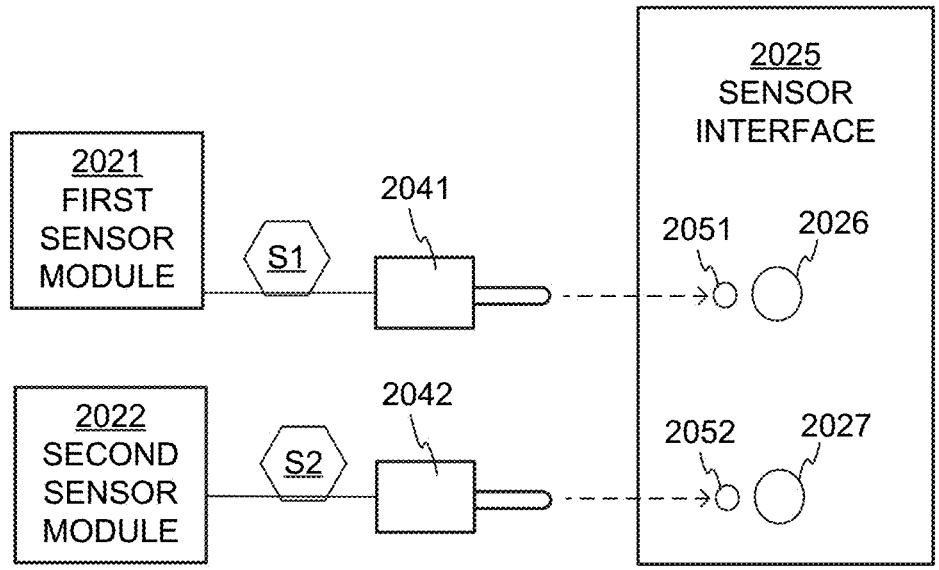
FIG. 20 is a diagram of a sample sensor interface configured to receive signals from two sensor modules concurrently according to embodiments.

FIG. 20 is a diagram of a sample sensor interface 2025. Sensor interface 2025 can be configured to receive signals S1, S2 from a first sensor module 2021 and a second sensor module 2022. Signals S1, S2 are received concurrently. In particular, sensor modules 2021, 2022 have respective plugs 2041, 2042. Sensor interface 2025 has two sockets 2051, 2052, that can receive plugs 2041, 2042 as shown.

Sensor interface 2025 also has a first visual indicator 2026 near socket 2051, which can be an LED or equivalent. Visual indicator 2026 is configured to indicate that signal S1 is being received via socket 2051, by being lit, and so on. Sensor interface 2025 further has a second visual indicator 2027 near socket 2052. Visual indicator 2027 is configured to indicate that signal S2 is being received via socket 2052.

In the example of FIG. 20, sockets 2051, 2052 are not shown as dedicated to sensor modules 2021, 2022. Plugs 2041, 2042 could have alternately been plugged in sockets 2052, 2051, respectively. A socket can be made dedicated to a plug, preferably by giving both of them custom complementary shapes, different for the other pairs of plugs/sockets. The patient would then find easy to match. Making them not dedicated may impose more requirements, for example either each signal would have to identify what parameter it is monitoring for further processing, or have the signal encode an alarm only, and the alarms could be uniform.

Sensor modules 2021, 2022 can monitor the same or a different parameter. For example they could both monitor motion, perhaps at different places of the patient's body. Identical motion patterns could then be attributed to environment, such as a mode of transportation, etc. Or one could monitor motion, and another blood flow, etc. In addition, embodiments could also be using a third sensor module, a fourth sensor module, and so on, in addition to the first two sensor modules.

Figure 21:
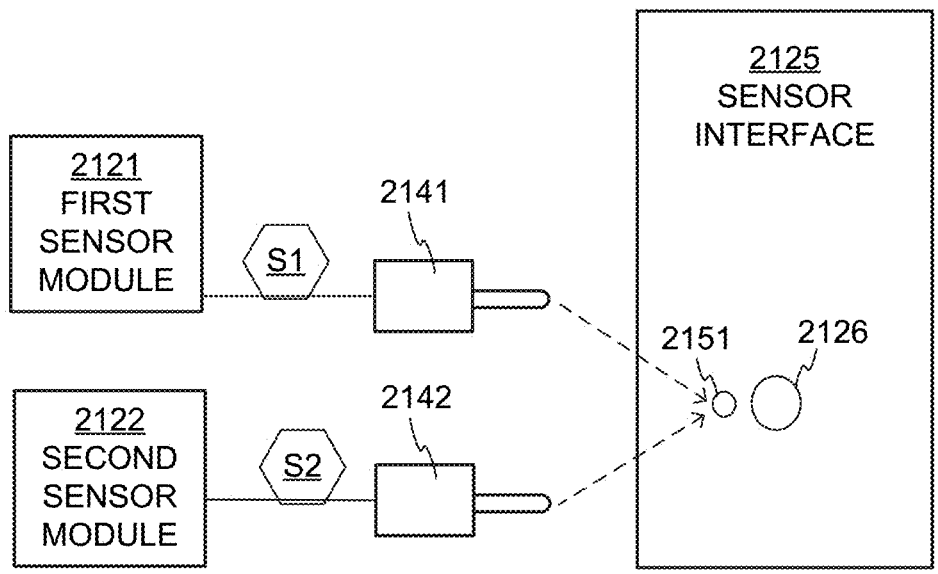
FIG. 21 is a diagram of a sample sensor interface configured to receive a signal from one of two sensor modules according to embodiments.

FIG. 21 is a diagram of a sample sensor interface 2125. Sensor interface 2125 has a socket 2151, and visual indicator 2126 configured to indicate that a signal is being received via socket 2151. Socket 2151 is not dedicated; it can receive either signal S1 from first sensor module 2121 via plug 2141, or signal S2 from second sensor module 2122 via plug 2142, depending on which sensor module the patient uses at the time.

In general, a sensor interface according to embodiments can receive the first and second signals in a number of ways. In some embodiments, these signals are received substantially periodically, for example every 10-60 sec. In some embodiments, the sensor interface can be configured to transmit a polling signal, and these signals can be received responsive to the sensor modules receiving the polling signal. Such a polling signal can be transmitted on a number of occasions. In some embodiments, the polling signal is transmitted substantially periodically, for example every 10-60 sec. In some embodiments, the polling signal is transmitted if one or more of the signals meets an alert condition.

Returning to FIG. 11, a WCD system according to embodiments may further include a processor 1130. Processor 1130 can be configured to make a determination 1140. Determination 1140 can be whether a certain severity threshold has been reached, and be made from signal S1 or from signal S2, or both, etc. This severity threshold may correspond or even be one of the thresholds of FIG. 2. In some embodiments, processor 330 performs determination 1140.

Determination 1140 may be performed in a number of ways, and be based on a number of criteria. In some embodiments, the certain severity threshold is reached if a signal from a sensor module is not received by a time it is expected. For example, such may be deemed to be the case if signal S1 has not been received for a first deadline duration time, in case of normally periodic receipt of the signal, or for a first deadline duration time after a polling signal has been transmitted. In such embodiments, the first escalation due to threshold may be to poll another sensor, or to activate user interface 370 and alert the wearer that the sensor module may have fallen off.

In some embodiments, if only one of signals S1 and S2 is received, processor 1130 is configured to determine whether the certain severity threshold has been reached from the signal that has been received, only. In some embodiments, even if both signals S1 and S2 are received, processor 1130 is configured to determine whether the certain severity threshold has been reached from only one of them. In some embodiments, processor 1130 is configured to determine whether the certain severity threshold has been reached from both signals S1 and S2. The determination of whether the threshold is reached or exceeded can be made as is known in the art. For example, in embodiments where a value is encoded in a voltage level, the determination can be made by a comparator that is tripped when the voltage level exceeds the applicable threshold voltage level. In other embodiments, the system can optionally include a logic device, such as a processor, and the value is encoded in as a number. The logic device can be is configured to determine when the parameter has reached or exceeded the appropriate threshold.

Figure 22:
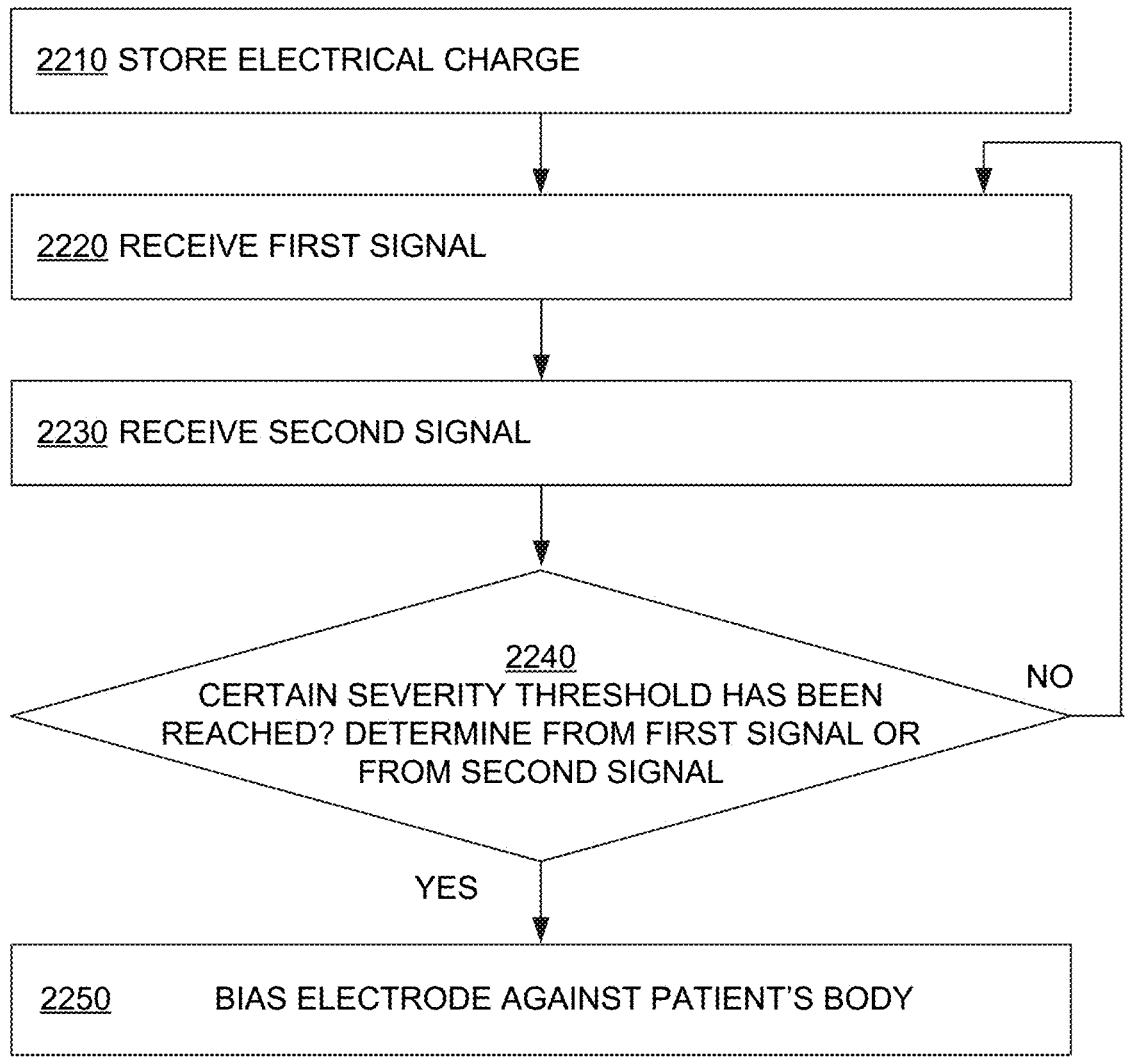
FIG. 22 is a flowchart for illustrating methods according to embodiments.

Additional methods are now described. FIG. 22 shows a flowchart 2200 for describing methods according to embodiments. These methods may also be practiced with additional operations, and by embodiments described above, for example a WCD system that includes a support structure and first electrodes coupled to the support structure such that, while the support structure is worn by the patient, at least a certain one of the first electrodes is moveable with respect to the patient's body responsive to the patient's moving.

According to an operation 2210, an electrical charge is stored.

According to another operation 2220, a first signal may be received. This first signal may have been made available from a first parameter of the patient that is monitored, and which is other than the patient's ECG. The first signal may be received periodically. Or, a poll signal may be transmitted and the first signal is received in response to the poll signal. The poll signal may be transmitted periodically, etc. as also described above.

According to another operation 2230, a second signal may be received. This second signal may have been made available from a second parameter of the patient that is monitored, and which is other the first parameter and other than the patient's ECG.

In embodiments, the WCD system further includes a first visual indicator, and an additional operation is to indicate, via the first visual indicator, that the first signal is being received. Same with a second visual indicator, etc. as described with reference to FIG. 20.

Returning to FIG. 22, according to another operation 2240, it may be determined from the first signal or from the second signal whether a certain severity threshold has been reached. This operation is akin to operation 1140, and may be performed as described above and in additional ways described later in this document.

If not, then execution may return to operation 2220. If yes, then according to another operation 2250, the certain electrode may be biased towards the patient's body against the support structure. This biasing may make the certain electrode becoming less moveable with respect to the patient's body than prior to biasing, and so on, as per the above.

In some embodiments, the WCD system further includes a user interface. An additional operation can be to issue a query to the patient via the user interface. In such embodiments, the certain or particular electrode may transition to the biased state only if a preset acceptable input has not been received in response to the query within a preset time after the query has been issued.

In some embodiments, the first electrodes are defibrillation electrodes. An additional operation can be discharging the stored electrical charge through the patient's body via the defibrillation electrodes, while the certain electrode is in the biased state.

In some embodiments, the first electrodes are ECG electrodes. An additional operation can be to receive an ECG reading of the patient via at least the certain electrode, while the certain electrode is in the biased state. In such embodiments, the WCD system further includes defibrillation electrodes. An additional operation can be to discharge the stored electrical charge through the patient's body via the defibrillation electrodes.

Additional ways are now described for performing operation 2240.

In one embodiment, FIG. 23 is a sample truth table 2340 for performing an operation 2240, in an example where three signals S1, S2, S3 are received from three sensor modules. Received signals S1, S2, S3 are used in a logic OR fashion, and the certain severity threshold is determined to be reached if any one of them is an alarm.

In another embodiment, FIG. 24 is a flowchart 2440 for performing operations 2220, 2230 and 2240. In this example three signals S1, S2, S3 may be received from three sensor modules, but any one of them not issuing an alarm does not cause the WCD system to alarm or escalate. After a start operation 2410, according to an operation 2410, an iteration counter ITC is set to 0. Subsequently, operations 2421, 2422, 2423 are stepped through as shown, each one for processing one of these signals. Each of these three operations 2421, 2422, 2423 has an entry node PA, and two exit nodes PB, PC. All exit nodes PC lead to operation 2499, which means exiting operation 2240 with the answer of "YES".

Internally, operations 2421, 2422, 2423 can be arranged as suitable. An example is now described for one of them which can be replicated for the other two.

FIG. 25 is a flowchart 2521 for illustrating a sample method for performing operation 2421 of FIG. 24 according to embodiments. According to an operation 2541, it is inquired whether signal S1 has been received timely.

If yes, then according to another operation 2542, iteration counter ITC is reset to zero. Then according to another operation 2543, it is inquired whether signal S1 is an alarm. If not, then execution may return to operation 2541. If yes, however, execution exits at node PC—an alarm has been registered.

If at operation 2541 the answer is NO, then according to another operation 2544, iteration counter ITC is incremented by one. Then, according to another operation 2545, it is inquired whether iteration counter ITC is larger than 2. The number 2 is derived because a total of three signals are being monitored.

If at operation 2545 the answer is NO, then execution exits at node PB, to reenter node PA for another sensor module. If at operation 2545 the answer is YES, execution exits at node PC—none of the sensor signals is being received timely.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet (ADS) of this patent application, are hereby incorporated by reference herein, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to choose similar though not identical reference numerals to denote versions or embodiments of an item, aspect, component or process that possibly similar or different. Where made, such a further effort was not required, but was nevertheless made gratuitously to accelerate comprehension by the reader. Even where made in this document, such an effort might not have been made completely consistently for all of the versions or embodiments that are made possible by this description. Accordingly, the description controls in defining the item, aspect, component or process, rather than its reference numeral. Any similarity in reference numerals may be used to infer a similarity in the text, but not to confuse aspects where the text or the context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A method for a Wearable Cardiac Defibrillator (WCD) system that is wearable by a patient who may be moving, the WCD system including a support structure that is worn by the patient, the WCD system further including first electrodes coupled to the support structure such that, while the support structure is worn by the patient, at least a certain one of the first electrodes is moveable with respect to the patient's body responsive to the patient's moving, the method comprising:
    transmitting a polling signal from a processor of the WCD system via a sensor interface to a first sensor module and to a second sensor module, wherein the first sensor module is configured to monitor a first parameter of the patient that is other than an electrocardiogram (ECG) of the patient, and the second sensor module is configured to monitor a second parameter of the patient that is other than the ECG of the patient;
    determining from a response of the first sensor module and from a response of the second sensor module whether a certain severity threshold has been reached, wherein said determining includes determining whether or not a first signal is received as the response of the first sensor module or a second signal is received as the response of the second sensor module responsive to the polling signal, and wherein said determining is based on a content of the first signal when the first signal received as the response and a content of the second signal when the second signal received as the response such that the certain severity threshold is determined to be reached when both the first signal and the second signal indicate the certain severity threshold has been reached; and
    biasing, responsive to determining that the certain severity threshold has been reached, the certain electrode towards the patient's body against the support structure, the certain electrode thereby becoming less moveable with respect to the patient's body than prior to biasing.

2. The method of claim 1, in which
the first electrodes are defibrillation electrodes, and further comprising:
storing an electrical charge; and
discharging the stored electrical charge through the patient's body via the defibrillation electrodes after biasing the certain electrode.

3. The method of claim 1, in which
the first electrodes are ECG electrodes, and further comprising:
receiving an ECG reading of the patient via at least the certain electrode after biasing the certain electrode.

4. The method of claim 3, in which
the WCD system further includes defibrillation electrodes, and further comprising
storing an electrical charge; and
discharging the stored electrical charge through the patient's body via the defibrillation electrodes.

5. The method of claim 1, in which
the polling signal is transmitted substantially periodically.

6. The method of claim 1, in which
the certain severity threshold is determined to be reached if the first signal has not been received for a first deadline duration time after the polling signal has been transmitted.

7. The method of claim 1, in which
the WCD system further includes a first visual indicator, and further comprising:
indicating, via the first visual indicator, that the first signal is being received.

8. The method of claim 7, in which
the WCD system further includes a second visual indicator, and further comprising:
indicating, via the second visual indicator, that the second signal is being received.

9. The method of claim 1, in which
if one of the first signal and the second signal stops being received, it is determined from the other of the first signal and the second signal whether the certain severity threshold has been reached.

10. The method of claim 1, in which
the WCD system further includes a user interface, and further comprising: issuing a query to the patient via the user interface, and
in which the certain electrode is biased only if a preset acceptable input has not been received from both the first sensor module and the second sensor module in response to the query within a preset time after the query has been issued.

11. The method of claim 1, in which
the first parameter of the patient is a sound of the patient.

12. A method for a wearable system that is wearable by a patient who may be moving, the wearable system including a support structure that is worn by the patient and a logic device, the wearable system configured for use with a first sensor module configured to monitor a sound made by the patient and to make available a first signal generated from the monitored sound, the wearable system further configured for use with a second sensor module configured to monitor another parameter of the patient that is neither the monitored sound nor the patient's electrocardiogram (ECG) and to make available a second signal generated from the other parameter, the method comprising:
transmitting a polling signal from the logic device to the first sensor module and to the second sensor module;
determining, by the logic device, from a response of the first sensor module and from a response of the second sensor module whether or not a certain severity threshold has been reached, wherein said determining includes determining whether or not the first signal is received as the response of the first sensor module or a second signal is received as the response of the second sensor module responsive to the polling signal, and wherein said determining is based on a content of the first signal when the first signal received as the response and a content of the second signal when the second signal received as the response such that the certain severity threshold is determined to be reached when both the first signal and the second signal indicate the certain severity threshold has been reached.

13. The method of claim 12, further comprising:
intervening, by the wearable system, responsive to determining that the certain severity threshold has been reached.

14. The method of claim 13, in which
the wearable system further includes first electrodes coupled to the support structure such that, while the support structure is worn by the patient, at least a certain one of the first electrodes is moveable with respect to the patient's body responsive to the patient's moving, and
the intervening includes biasing the certain electrode towards the patient's body against the support structure, the certain electrode thereby becoming less moveable with respect to the patient's body than prior to becoming thus biased.

15. The method of claim 14, in which
the first electrodes are defibrillation electrodes, and further comprising:
storing an electrical charge; and
discharging the stored electrical charge through the patient's body via the defibrillation electrodes.

16. The method of claim 14, in which
the first electrodes are ECG electrodes, and further comprising:
receiving an ECG reading of the patient via at least the certain electrode.

17. The method of claim 16, in which the wearable system further includes defibrillation electrodes, and further comprising:
storing an electrical charge; and
discharging the stored electrical charge through the patient's body via the defibrillation electrodes.

18. The method of claim 14, in which
the wearable system further includes a user interface, and further comprising: issuing a query to the patient via the user interface, and
in which the certain electrode becomes biased only if a preset acceptable input has not been received in response to the query within a preset time after the query has been issued.

19. The method of claim 12, in which
if one of the first signal and the second signal stops being received, it is determined from the other of the first signal and the second signal whether the certain severity threshold has been reached.

20. The method of claim 12, in which
the certain severity threshold is determined to be reached if the first signal has not been received from the first sensor module and the second sensor module for a first deadline duration time.

21. A method for a wearable system that is wearable by a patient who may be moving, the wearable system including a support structure that is worn by the patient and a logic device, the wearable system configured for use with a first sensor module configured to monitor a sound made by the patient and to make available a first signal generated from the monitored sound, and for use with a second sensor module configured to monitor another parameter of the patient that is not an electrocardiogram (ECG) signal and to make available a second signal from the patient parameter, the method comprising:
transmitting a polling signal from the logic device to the first sensor module and the second sensor module; and
determining, by the logic device, from a response of the first sensor module and the second sensor module whether or not a certain severity threshold has been reached, wherein said determining includes determining whether or not a signal is received from both the first sensor module and the second sensor module as the response of the sensor modules responsive to the polling signal, and wherein said determining is based on a content of the signals when the signals are received as the response such that the certain severity threshold is determined to be reached when the signals from both the first sensor module and the second sensor module indicate the certain severity threshold has been reached.

22. The method of claim 21, further comprising;
intervening, by the wearable system, responsive to determining that the certain severity threshold has been reached.

23. The method of claim 22, in which
the wearable system further includes first electrodes coupled to the support structure such that, while the support structure is worn by the patient, at least a certain one of the first electrodes is moveable with respect to the patient's body responsive to the patient's moving, and
the intervening includes biasing the certain electrode towards the patient's body against the support structure, the certain electrode thereby becoming less moveable with respect to the patient's body than prior to becoming thus biased.

24. The method of claim 23, in which
the first electrodes are defibrillation electrodes, and further comprising: storing an electrical charge; and
discharging the stored electrical charge through the patient's body via the defibrillation electrodes.

25. The method of claim 23, in which
the first electrodes are ECG electrodes, and further comprising:
receiving an ECG reading of the patient via at least the certain electrode.

26. The method of claim 25, in which
the wearable system further includes defibrillation electrodes, and further comprising: storing an electrical charge; and
discharging the stored electrical charge through the patient's body via the defibrillation electrodes.

\* \* \* \* \*